US009862972B2

(12) United States Patent
Picker et al.

(10) Patent No.: US 9,862,972 B2
(45) Date of Patent: Jan. 9, 2018

(54) CMV GLYCOPROTEINS AND RECOMBINANT VECTORS

(71) Applicant: Oregon Health & Science University, Portland, OR (US)

(72) Inventors: Louis Picker, Portland, OR (US); Klaus Früh, Portland, OR (US); Scott Hansen, Portland, OR (US)

(73) Assignee: Oregon Health & Science University, Portland, OR (US)

( * ) Notice: Subject to any disclaimer, the term of this patent is extended or adjusted under 35 U.S.C. 154(b) by 0 days.

(21) Appl. No.: 14/086,602

(22) Filed: Nov. 21, 2013

(65) Prior Publication Data

US 2014/0141038 A1    May 22, 2014

Related U.S. Application Data

(63) Continuation of application No. PCT/US2012/041475, filed on Jun. 8, 2012.

(60) Provisional application No. 61/495,552, filed on Jun. 10, 2011.

(51) Int. Cl.
| | |
|---|---|
| C12N 15/86 | (2006.01) |
| C12N 7/00 | (2006.01) |
| A61K 39/12 | (2006.01) |
| A61K 39/00 | (2006.01) |

(52) U.S. Cl.
CPC ............ *C12N 15/86* (2013.01); *A61K 39/12* (2013.01); *C12N 7/00* (2013.01); *A61K 2039/5256* (2013.01); *C12N 2710/16121* (2013.01); *C12N 2710/16143* (2013.01); *C12N 2740/15034* (2013.01); *C12N 2740/15071* (2013.01); *C12N 2800/204* (2013.01)

(58) Field of Classification Search
CPC .. A61K 39/12; A61K 39/245; A61K 39/0011; A61K 2039/5254; A61K 39/00; A61K 38/00; A61K 39/39558; A61K 2039/70; A61K 2039/525; A61K 35/763; C12N 7/00; C12N 15/86; C12N 2710/16143; C12N 2710/16162; C12N 2710/16121; C12N 2710/16634; C12N 2710/16111; C12N 2710/16171; C12N 2710/16622; C12N 2710/16122; C12N 2710/16141; C12N 2710/16152; C12N 2710/16632; C12N 15/869; C12N 5/0636; C12N 5/0638; C12N 2710/16011
See application file for complete search history.

(56) References Cited

U.S. PATENT DOCUMENTS

| | | | |
|---|---|---|---|
| 5,273,876 A | 12/1993 | Hock et al. | |
| 5,720,957 A | 2/1998 | Jones et al. | |
| 5,830,745 A | 11/1998 | Hock et al. | |
| 6,033,671 A | 3/2000 | Frueh et al. | |
| 7,892,822 B1 | 2/2011 | Koszinowski et al. | |
| 2002/0176870 A1 | 11/2002 | Schall et al. | |
| 2003/0118568 A1* | 6/2003 | Crew | 424/93.21 |
| 2004/0086489 A1 | 5/2004 | Schall et al. | |
| 2004/0248300 A1 | 12/2004 | Preston | |
| 2005/0064394 A1 | 3/2005 | Liu et al. | |
| 2005/0118192 A1 | 6/2005 | Boursnell et al. | |
| 2006/0019369 A1 | 1/2006 | Hahn | |
| 2008/0199493 A1* | 8/2008 | Picker et al. | 424/208.1 |
| 2009/0148477 A1 | 6/2009 | Bruder et al. | |
| 2009/0203144 A1 | 8/2009 | Beaton et al. | |
| 2009/0297555 A1 | 12/2009 | Kemble et al. | |
| 2013/0136768 A1* | 5/2013 | Picker et al. | 424/199.1 |
| 2013/0142823 A1* | 6/2013 | Picker et al. | 424/199.1 |
| 2013/0156808 A1 | 6/2013 | Jonjic | |
| 2013/0202638 A1* | 8/2013 | Thirion et al. | 424/229.1 |

FOREIGN PATENT DOCUMENTS

| | | |
|---|---|---|
| EP | 0521427 A1 | 1/1993 |
| WO | 1988/10311 A1 | 12/1988 |
| WO | 1996/04383 A1 | 2/1996 |
| WO | 2002/062296 A2 | 8/2002 |
| WO | 2006/031264 A2 | 3/2006 |
| WO | 2011/093858 A1 | 8/2011 |
| WO | WO 2011-119920 A2 | 9/2011 |
| WO | 2011/138040 A2 | 11/2011 |
| WO | 2011/143653 A2 | 11/2011 |

OTHER PUBLICATIONS

Brondke H. Human herpesvirus 5, Towne Strain. US6 (NCBI GenBank Acc. No. AAS49004), Dep. Apr. 8, 2004.*
Brondke H. Human herpesvirus 5, Towne Strain. US3 (NCBI GenBank Acc. No. AAS49002). Dep. Apr. 8, 2004.*
Hansen, S.G. et al., "Evasion of CD8+ T cells critical for superinfection by cytomegalovirus", Science, vol. 328 (102), pp. 102-106 (Apr. 2, 2010).
Davison et al., "New Genes from Old: Redeployment of dUTPase by Herpesviruses," Journal of Virology, Oct. 2005, vol. 79, No. 20, pp. 12880-12892.
Bresnahan, Wade et al., "UL82 Virion Protein Activates Expression of Immediate Early Viral Genes in Human Cytomegalovirus-Infected Cells," Proc Nat Acad Sci, Dec. 19, 2000, vol. 97, No. 26, pp. 14506-14511.
Schleiss, Mark R. et al., "Genetically Engineered Live-attenuated Cytomegalovirus (CMV) Vaccines Improve Pregnancy Outcome in the Guinea-pig Model of Congenital CMV Infection," Retrovirology, Apr. 2008, vol. 5, Suppl I, pp. 1-3.
Mahmood, Kutubuddin et al., "Human Cytomegalovirus Plasmid-based Amplicon Vector System for Gene Therapy," Genetic Vaccines and Therapy, Jan. 26, 2005, vol. 3, No. 1:1.

(Continued)

*Primary Examiner* — Rachel B Gill
(74) *Attorney, Agent, or Firm* — Schwabe, Williamson & Wyatt, P.C.

(57) ABSTRACT

Disclosed herein are recombinant CMV vectors which may comprise a heterologous antigen that can repeatedly infect an organism while inducing a CD8+ T cell response to immunodominant epitopes of the heterologous antigen. The CMV vector may comprise a deleterious mutation in the US11 glycoprotein or a homolog thereof.

55 Claims, 18 Drawing Sheets

(56) References Cited

OTHER PUBLICATIONS

Mohr, Christian A. et al., "A Spread-Deficient Cytomegalovirus for Assessment of First-Target Cells in Vaccination," Journal of Virology, Aug. 2010, vol. 84, No. 15, pp. 7730-7742.
Mohr, Christian A. et al., "Engineering of Cytomegalovirus Genomes for Recombinant Live Herpesvirus Vaccines," International Journal of Medical Microbiology, 2008, vol. 298, pp. 115-125.
Murphy, Eain et al., "Coding Potential of Laboratory and Clinical Strains of Human Ctyomegalovirus," Proc Nat Acad Sci, Dec. 9, 2003, vol. 100, No. 25, pp. 14976-14981.
Onuffer, James J. et al., "Chemokines, Chemokine Receptors and Small-molecule Antagonists: Recent Developments," Trends in Pharmacological Sciences, Oct. 2002, vol. 23, No. 10, pp. 459-467.
Redwood, Alec J. et al., "Use of a Murine Cytomegalovirus K181-Derived Bacterial Artificial Chromosome as a Vaccine Vector for Immunocontraception," Journal of Virology, Mar. 2005, vol. 79, No. 5, pp. 2998-3008.
Tessmer, Marlowe S. et al., "Salivary Gland NK Cells are Phenotypically and Functionally Unique," PLoS Pathogens, Jan. 2011, vol. 7, Issue 1, pp. 1-9.
Powers, Colin et al., "Rhesus CMV: An Emerging Animal Model for Human CMV," Med Microbiol Immunol., Jun. 2008, vol. 197, No. 2, pp. 109-115.
Campadelli-Flume, et al., Editors, "Chapter 15: Betaherpes Viral Genes and Their Functions" Human Herpesviruses: Biology, Therapy, and Immunoprophylaxis. Cambridge: Cambridge University Press, 2007.
Basta, Sameh, et al., "Inhibitory Effects of Cytomegalovirus Proteins US2 and US11 Point to Contributions from Direct Priming and Cross-Priming in Induction of Vaccinia Virus-Specific CD8+ T Cells," The Journal of Immunology, 2002, vol. 168, pp. 5403-5408.
Jones, Thomas R. et al., "Replacement Mutagenesis of the Human Cytomegalovirus Genome: US10 and US11 Gene Products are Nonessential," Journal of Virology, Nov. 1991, vol. 65, No. 11, pp. 5860-5872.
Wiertz, Emmanuel J.H. J. et al, "The Human Cytomegalovirus US11 Gene Product Dislocates MHC Class I Heavy Chains from the Endoplasmic Reticulum to the Cytosol," Cell, Mar. 8, 1996, vol. 84, pp. 769-779.
Jones, Thomas R. et al., "Multiple Independent Loci Within the Human Cytomegalovirus Unique Short Region Down-Regulate Expression of Major Histocompatibility Complex Class I Heavy Chains," Journal of Virology, Aug. 1995, vol. 69, No. 8, pp. 4830-4841.
Chau, Nha H. et al., "Transcriptional Regulation of the Human Cytomegalovirus US11 Early Gene," Journal of Virology, Feb. 1999, vol. 73, No. 2, pp. 863-870.
Besold, K. et al., "Immune Evasion Proteins gpUS2 and gpUS11 of Human Cytomegalovirus Incompletely Protect Infected Cells from CD8 T Cell Recognition," Virology, Jun. 30, 2009, vol. 391, pp. 5-19.
Chang, W.L. et al., "Cloning of the Full-Length Rhesus Ctyomegalovirus Genome as an Infectious and Self-Excisable Bacterial Artificial Chromosome for Analysis of Viral Pathogenesis," Journal of Virology, May 2003, vol. 77, No. 9, pp. 5073-5083.
Hansen, S.G. et al., "Profound Early Control of Highly Pathogenic SIV by an Effector Memory T-cell Vaccine," Nature, May 26, 2011, vol. 473, pp. 523-530.
Grimwood, J. et al., "NCBI GenBank Direct Submission," Acc. No. AC146906, Sub. Nov. 5, 2003.
"Oxxon Terapeutics Licenses Rights to Xenova's DISC-HSV and DISC-GM-CSF Vector Technolgies," BusinessWire, Jan. 13, 2005.
Dudek, Tim et al., "Replication-defective Viruses as Vaccines and Vaccine Vectors," Virology, 2006, vol. 344, pp. 230-239.

Mc Gregor, Alistair et al., Molelcular, Biological, and In Vivo Characterization of the Guinea Pig Cytomegalovirus (CMV) Homologs of the Human CMV Matrix Proteins pp71 (UL82) and pp65 (UL83), Journal of Virology, Sep. 2004, vol. 78, No. 18, pp. 9872-9889.
Lilja, Anders E. et al., "Functional Genetic Analysis of Rhesus Cytomegalovirus: Rh01 is an Epithelial Cell Tropism Factor," Journal of Virology, Mar. 2008, vol. 82, No. 5, pp. 2170-2181.
Dunn, Walter, et al., "Functional Profiling of a Human Cytomegalovirus Genome," Proc Natl Acad Sci, Nov. 25, 2003, vol. 100, No. 24, pp. 14223-14228.
Cantrell, Stacy R. et al., "Interaction Between the Human Cytomegalovirus UL82 Gene Product (pp71) and hDaxx Regulates Immediate-Early Gene Expression and Viral Replication," Journal of Virology, Jun. 2005, vol. 79, No. 12, pp. 7792-7802.
Bresnahan, Wade et al., "Replication of Wild-Type and Mutant Human Cyomegalovirus in Life-Extended Human Diploid Fibroblasts," Journal of Virology, Nov. 2000, vol. 74, No. 22, pp. 10816-10818.
Cantrell, Stacy R. et al., "Human Cytomegalovirus (HCMV) UL82 Gene Product (pp71) Relieves hDaxx-Mediated Repression of HMCV Replication," Journal of Virology, Jun. 2006, vol. 80, No. 12, pp. 6188-6191.
Moutaftsi, Magdalena et al., "Human Cytomegalovirus Inhibits Maturation and Impairs Function of Monocyte-derived Dendritic Cells," Blood, Apr. 15, 2002, vol. 99, No. 8, pp. 2913-2921.
Gorman, Shelley et al., "Prior Infection with Murine Cytomegalovirus (MCMC) limits the Immunocontraceptive Effects of an MCMV Vector Expressing the Mouse-zona-pellucida-3 Protein," Vaccine, Jun. 2008, vol. 26, pp. 3860-3869.
Plotkin, Stanley A. et al., "Vaccines for the Prevention of Human Cytomegalovirus Infection," Reviews of Infectious Diseases, Sep.-Oct. 1990, vol. 12, Supplement 7, pp. S827-S838.
Olaleye, O.D. et al., "Cytomegalovirus Infection Among Tuberculosis Patients in a Chest Hospital in Nigeria," Comp. Immun. Microbiol. Infect. Dis. 1990, vol. 13, No. 2, pp. 101-106.
Kaech, Susan M. et al., "Effector and Memory T-Cell Differentiation: Implications for Vaccine Development," Nature Reviews, Apr. 2002, vol. 2 pp. 251-262.
Halary, Franck et al., "Human Cytomegalovirus Binding to DC-SIGN is Required for Dendritic Cell Infection and Target Cell trans-Infection," Immunity, Nov. 2002, vol. 17, pp. 653-664.
Marshall, Ker R. et al., "Activity and Intracellular Localization of the Human Cytomegalovirus Protein pp71," Journal of General Virology, Mar. 2002, vol. 83, pp. 1601-1612.
Kalejta, Robert F. et al., "Human Cytomegalovirus pp71: A New Viral Tool to Probe the Mechanisms of Cell Cyle Progression and the Oncogenesis Controlled by the Retinoblastoma Family of Tumor Suppressors," Journal of Cellular Biochemistry, Apr. 2004, vol. 93, pp. 37-45.
Borst, Eva Maria et al., "Construction of a Cytomegalovirus-Based Amplicon: A Vector with a Unique Transfer Capacity," Human Gene Therapy, Jul. 1, 2003, vol. 14, pp. 959-970.
Ulmer, Jeffrey B., "Tuberculosis DNA Vaccines," Scandinavian Journal of Infectious Disease, 2001, vol. 33, pp. 246-248.
Wang, Xiuqing et al., "Murine Cytomegalovirus Abortively Infects Human Dendritic Cells, Leading to Expression and Presentation of Virally Vectored Genes," Journal of Virology, Jul. 2003, vol. 77, No. 13, pp. 7182-7192.
Hansen, Scott G. et al., "Effector Memory T Cell Responses are Associated with Protection of Rhesus Monkeys from Mucosal Simian Immunodeficiency Virus Challenge," Nature Medicine, Mar. 2009, vol. 15, No. 3, pp. 293-312.
Borst, E et al., "Development of a Cytomegalovirus Vector for Somatic Gene Therapy," Bone Marrow Transplantation, 2000, vol. 25, Supp. 2, pp. S80-S82.
Karrer et al., "Expansion of Protective CD8+ T-Cell Responses Driven by Recombinant Cytomegaloviruses," Journal of Virology, Mar. 2004, vol. 78, No. 5, pp. 2255-2264.
Murphy, Cynthia G. et al.,"Vaccine Protection against Simian Immunodeficiency Virus by Recombinant Strains of Herpes Simplex Virus," Journal of Virology, Sep. 2000, vol. 74, No. 17, pp. 7745-7754.

(56) References Cited

OTHER PUBLICATIONS

Rizvanov, Albert et al., "Generation of a Recombinant Cytomegalovirus for Expression of a Hantavirus Glycoprotein," Journal of Virology, 2003, vol. 77, No. 22, pp. 12203-12210.

Hansen, Scott G., et al., "Complete Sequence and Genomic Analysis of Rhesus Cytomegalovirus," Journal of Virology, Jun. 2003, vol. 77, No. 12, pp. 6620-6636.
Hagemeier, SC, "Functional Analysis of the Human Cytomegalovirus UL82 Gene Product PP71 During Virus Replication," Doctoral Dissertation, The University of Texas Southwestern Medical at Dallas, May 2007, pp. 1-181.
Ryckman, Brent J. et al., "Characterization of the Human Cytomegalovirus gH/gL/US128-131 Complex That Mediates Entry into Epithelian and Endothelial Cells," Journal of Virology, Jan. 2008, vol. 82, No. 1, pp. 60-70.
Oxford, Kristie et al., "Protein Coding Content of the ULb' Region of Wild-type Rhesus Cytomegalovirus," Virology, Mar. 30, 2008, vol. 373, No. 1, pp. 181-183.
Hahn, Gabriele et al., "Human Cytomegalovirus UL 131-128 Genes are Indispensible for Virus Growth in Endothelial Cells and Virus Transfer to Leukocytes," Journal of Virology, Sep. 2004, vol. 78, No. 18, pp. 10023-10033.

* cited by examiner

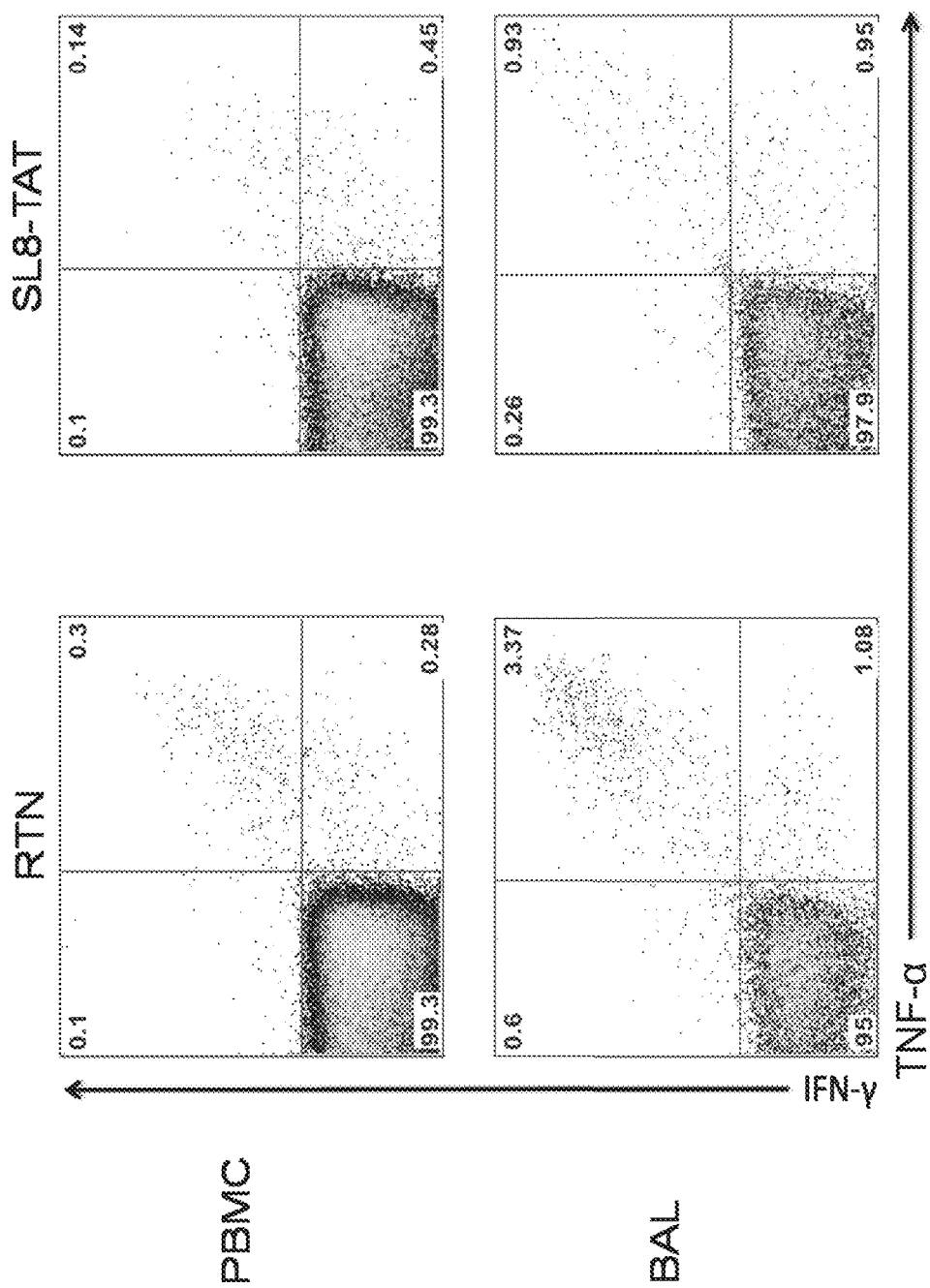

CMV GLYCOPROTEINS AND RECOMBINANT VECTORS

RELATED APPLICATIONS AND INCORPORATION BY REFERENCE

This application is a continuation application of international patent application Serial No. PCT/US12/41475 filed Jun. 8, 2012, which published as PCT Publication No. WO 2012/170765 on Dec. 13, 2012, which claims benefit of and priority to U.S. provisional patent application Ser. No. 61/495,552, filed 10 Jun. 2011. Reference is made to international patent application Ser. No. PCT/US11/29930 filed Mar. 25, 2011, U.S. provisional patent application Ser. No. 60/317,647 filed Mar. 25, 2010 and U.S. patent application Ser. No. 11/597,457 filed Apr. 28, 2008.

FEDERAL FUNDING LEGEND

This invention was supported in part by the National Institutes of Health grant number RO1 AI059457. The federal government may have certain rights to this invention.

The foregoing applications, and all documents cited therein or during their prosecution and all documents cited or referenced in the application, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

This invention relates to recombinant cytomegalovirus vectors, methods of making them, uses for them, expression products from them, and uses thereof. This invention also relates to cytomegalovirus glycoproteins US2 to US11, in particular recombinant cytomegalovirus vectors lacking one or more of the glycoproteins US2 to US11, particularly US8 to US11, and more particularly, US11.

BACKGROUND OF THE INVENTION

HCMV is an ubiquitous virus that is present in over 60% of the population depending on socioeconomic status. Following primary infection, HCMV persists for the life span of the host. Although HCMV is generally benign in healthy individuals, the virus can cause devastating disease in immunocompromised populations resulting in high morbidity and mortality (for review, see (Pass, R. F. 2001. Cytomegalovirus, p. 2675-2705. In P. M. H. David M. Knipe, Diane E. Griffin, Robert A. Lamb, Malcolm A. Martin, Bernard Roizman and Stephen E. Straus (ed.), Fields Virology, 4th ed. Lippincott Williams & Wilkins, Philadelphia, incorporated by reference herein).

CMV is one of the most immunogenic viruses known. High antibody titers are directed against numerous viral proteins during primary infection of healthy individuals (Alberola, J et al., J Clin Virol 16, 113-122 (2000); Rasmussen L et al., J Infect Dis 164, 835-842 (1991); and (Farrell H E and Shellam G R, J Gen Virol 70 2573-2586 (1989), all of which are incorporated by reference herein. In addition, a large proportion of the host T cell repertoire is also directed against CMV antigens, with 5-10 fold higher median CD4+ T cell response frequencies to HCMV than to acute viruses (measles, mumps, influenza, adenovirus) or even other persistent viruses such as herpes simplex and varicella-zoster viruses (Sylwester A W et al., J Exp Med 202, 673-685 (2005). A high frequency of CD8+ responses to defined HCMV epitopes or proteins is also commonly observed (Gillespie G M et al., J Virol 74, 8140-8150 (2000), Kern F et al., J Infect Dis 185, 1709-1716 (2002), Kern F et al., Eur J Immunol 29, 2908-2915 (1999), Kern F et al., J Virol 73, 8179-8184 (1999) and Sylwester A W et al., J Exp Med 202, 673-685 (2005). In a large-scale human study quantifying CD4+ and CD8+ T cell responses to the entire HCMV genome, the mean frequencies of CMV-specific CD4+ and CD8+ T cells exceeded 10% of the memory population for both subsets and in some individuals, CMV-specific T cells to account for >25% of the memory T cell repertoire.

Paradoxically, the robust immune response to CMV is unable to either eradicate the virus from healthy infected individuals or confer protection against re-infection. This ability of CMV to escape eradication by the immune system, and to re-infect the sero-positive host has long been believed to be linked to the multiple viral immunomodulators encoded by the virus (for review, see Mocarski E S et al., Trends Microbiol 10, 332-339 (2002) incorporated by reference herein.) The HCMV US6 family of proteins (equivalent to RhCMV homologues: Rh182-Rh189) are the most extensively studied of these immunomodulators (Loenen W A et al., Semin Immunol 13, 41-9 (2001); incorporated by reference herein.) At least four different genes, US2, US3, US6 and US11—and the respective RhCMV homologues (Rh182, Rh184, Rh185, and Rh189)—are known to interfere with assembly and transport of MHC I molecules (Ahn K et al., Proc Natl Acad Sci USA 93, 10990-10995 (1996), Ahn K et al., Immunity 6, 613-621 (1997.) Jones T R et al., J Virol 69, 4830-4841 (1995); Pande N T et al., J Virol 79, 5786-5798, (2005). Wiertz E J et al., Cell 84, 769-779 (1996); and Wiertz E J et al., Nature 384, 432-438 (1996); all of which are incorporated by reference herein.)

Each of these four molecules interferes at different essential points of MHC I protein maturation. US2 binds to newly synthesized MHC I heavy chain (HC) and reverse translocates the protein through the translocation channel SEC61 back into the cytosol where HC is degraded by the proteasome. Similarly, US11 ejects MHC I back out into the cytoplasm. US3 and US6 act later in the MHC-I assembly process with US3 retaining fully formed heterotrimers in the ER thus preventing their transport to the cell surface and US6 preventing peptide transport by TAP and thus formation of the trimeric complex of HC, β2 m and peptide.

CMV-based vectors expressing heterologous antigens do not induce cytotoxic T cells directed against immunodominant epitopes of those heterologous antigens. This limits the efficacy of the T cells raised by a CMV-based vaccine to protect against infection by a pathogen or mount a cellular immune response against a tumor.

However, CMV-based vectors lacking viral inhibitors of antigen presentation by MHC class I molecules—CMV based vectors that have deleterious mutations in (including deletion of) all of US2, US3, US6, US8, US10, and US11 (ΔUS2-11 vectors) do indeed induce T cells to respond to immunodominant antigens. (Hansen S G et al., Science 328, 102-106 (2010). However, wild type US2, US3, US6, US8, US10, and US11 confer superinfectivity in wild-type CMV vectors. Therefore vectors that have deleterious mutations in all of US2, US3, US6, US8, US10, and US11 are eliminated by cytotoxic CD8+ T cells in individuals previously inoculated with CMV-vectors or naturally infected with CMV. Because the vast majority of humans have been exposed to CMV at some point in their lives, CMV based vectors that have deleterious mutations in all of US2, US3, US6, US8, US10, and US11 would be of limited use.

The ability of wild type CMV to super-infect CMV-immune individuals and its inability to induce cytotoxic CD8+ T cells to immunodominant epitopes of heterologous antigens was thought to be intricately linked. Immunogenicity of CMV vectors was only be improved at the cost of losing the ability to super-infect.

There is a need for CMV vectors that are able to super-infect CMV-immune individuals and induce an immune response, for example, cytotoxic CD8+ T cells.

Citation or identification of any document in this application is not an admission that such document is available as prior art to the present invention.

SUMMARY OF THE INVENTION

The present invention relates to viral vectors that overcome a crucial shortcoming in the development of vaccines based on cytomegalovirus (CMV).

The present invention relates to vectors that may have mutations (up to and including whole deletions) of the US8, US10, and US11 genes, but that maintain functional homologues of US2, US3, and US6. These vectors may be useful in patients with prior CMV immunity, and generate a cytotoxic T-cell response to immunodominant epitopes of heterologous antigens.

The present invention relates to HCMV vectors that have deleterious mutations in, up to and including complete deletions of one or more HCMV glycoproteins. Such mutated glycoproteins include deleterious mutations of one or more of US8, US10, or US (or functional homologues thereof) while leaving functional copies of US2-US6 (or functional homologues thereof). In further examples, the HCMV vector may comprise a deleterious mutation, up to and including a complete deletion of US11, with functional copies of one or more of US2, US3, US6, US8, and US10 remaining in the vector.

The present invention also relates to a method of generating an immune response to a CMV heterologous antigen in a subject which may comprise administering a CMV vector with a deleterious mutation in at least one of US8, US10 or US11 or a functional homologue thereof and wherein the CMV vector contains and expresses a heterologous antigen. The heterologous antigen may be any antigen, including pathogen-derived or cancer-derived antigens, including HIV antigens.

The applicants intend not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

BRIEF DESCRIPTION OF THE DRAWINGS

The following detailed description, given by way of example, but not intended to limit the invention solely to the specific embodiments described, may best be understood in conjunction with the accompanying drawings.

FIG. 10 is a flow diagram of cells responding to RTN and its immunodominant peptide SL8-tat in a rhesus macaque inoculated with RhCMV/RTNA189gag, showing that a deleterious mutation in US11 alone is sufficient to confer superinfectivity and presentation of immunodominant epitopes.

DETAILED DESCRIPTION OF THE INVENTION

The invention relates to a CMV vector capable of repeatedly infecting an organism which may comprise a deleterious mutation in the glycoprotein US11 of such a character that the mutation renders the particular glycoprotein non-functional or causes a reduction in function. The mutation may be any mutation, including a point mutation, a frameshift mutation, and a deletion of less than all of the glycoprotein, the deletion of the entire glycoprotein, or the deletion of the nucleic acid sequence encompassing all of US8, US10, and US11 and all intervening sequences. In further examples, the CMV vector may comprise a deleterious mutation in US11, up to and including the deletion of all of the US11 ORF.

Figure 6A:
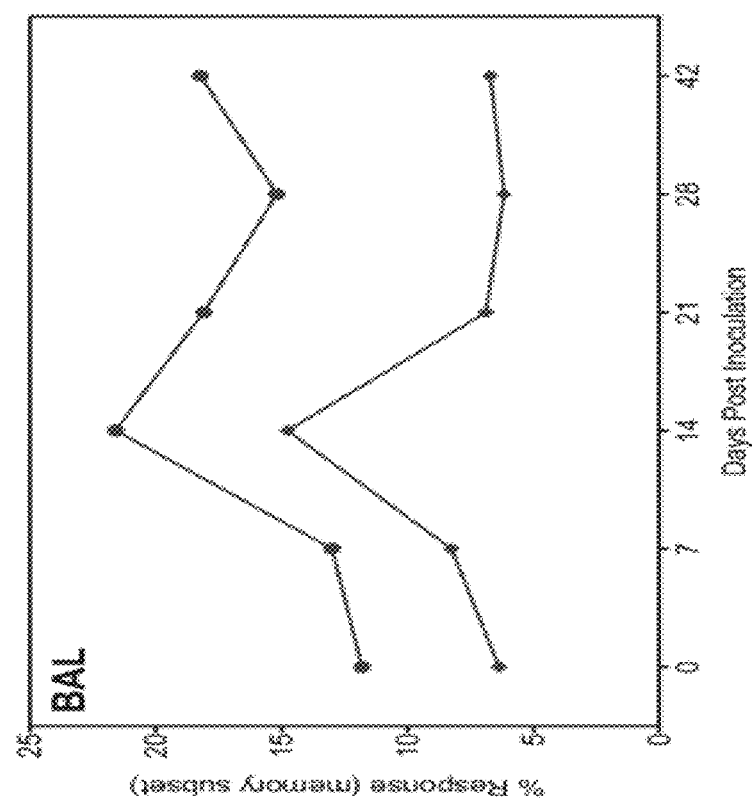
FIG. 6A depicts the boosted RhCMV-specific CD4+ T cell response in PBMC and BAL. Boosting of pre-existing anti-CMV T cell responses are a sign of super-infection by the incoming vector.
Figure 6A:
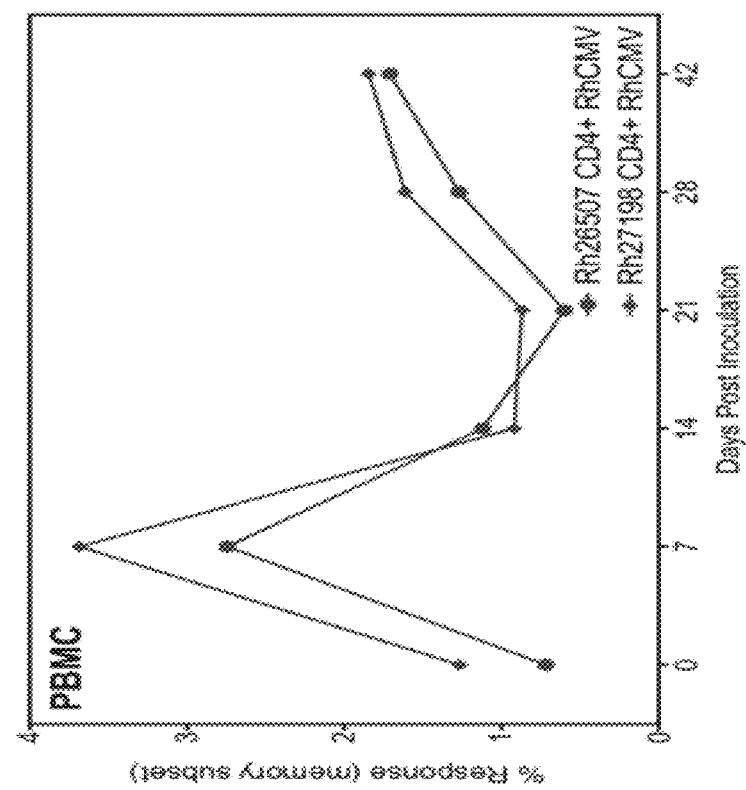
Figure 6B:
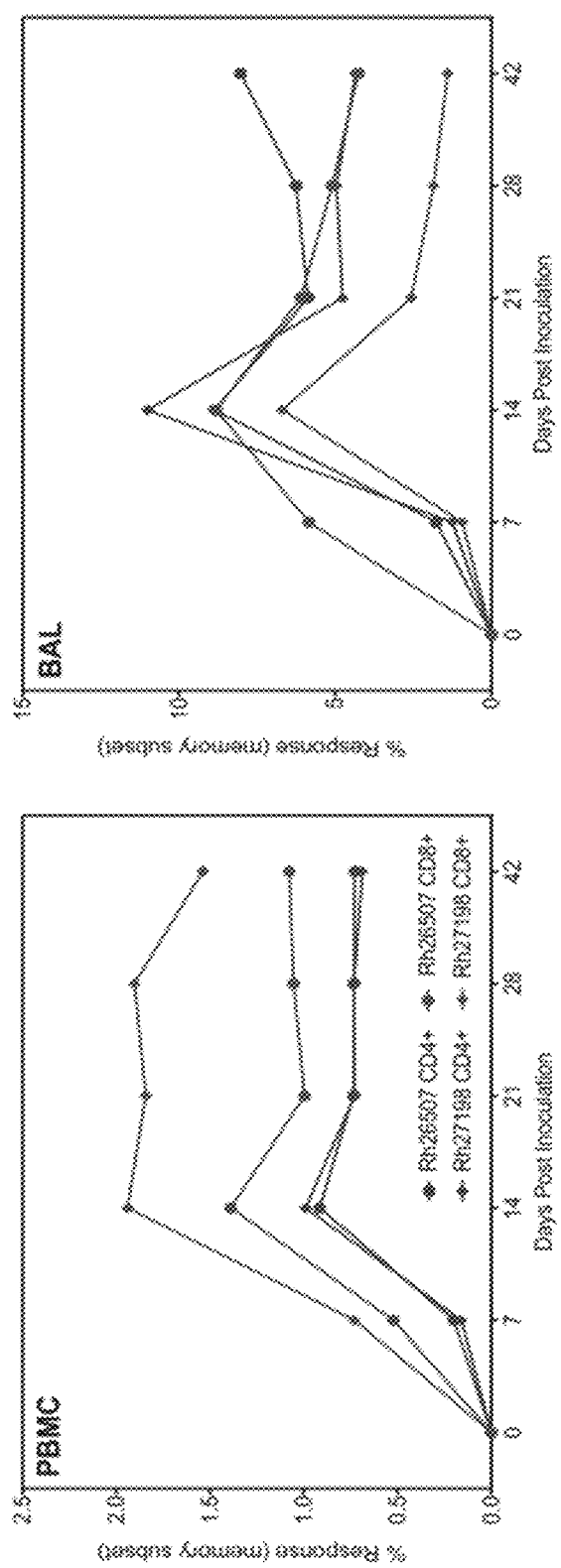
FIG. 6B depicts the development of total SIVgag-specific CD4+ and CD8+ T cell response in PBMC and BAL. The development of a de novo SIVgag response is proof for super-infection.
Figure 6C:
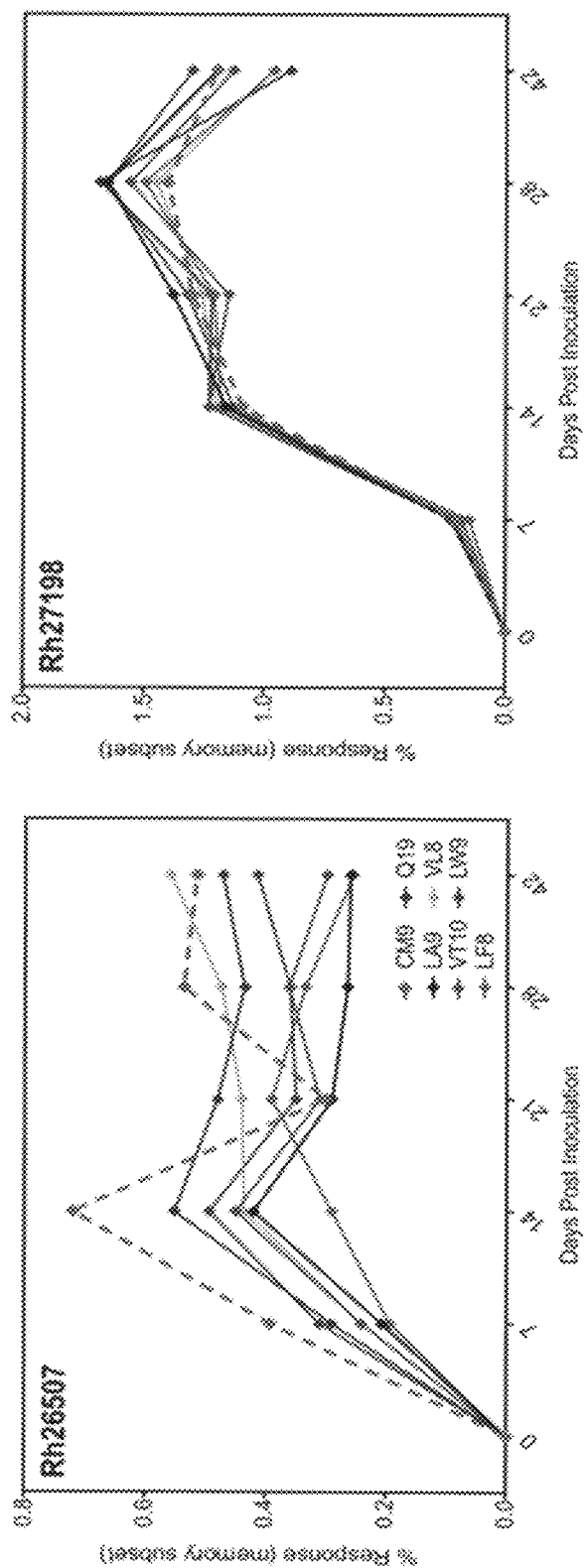
FIG. 6C depicts the development of CD8+ T cell response in PBMC to specific SIVgag-derived peptides that are known Mamu A*01-restricted epitopes. The development of T cell responses against immunodominant epitopes is in contrast to the lack of these responses upon super-infection with wild-type RhCMV expressing gag (FIG. 1).

For example, FIGS. 6A, 6B and 6C show that a viral vector with a deletion of US8-11 is still capable of super-infection of CMV-positive animals and that CMV lacking US8-11 induces a T cell response to immunodominant SIV epitopes. Two CMV-positive rhesus macaques (RM) (#26597 & #27198) were inoculated subcutaneously with $10^7$ PFU of recombinant ΔUS8-11gag. Responses frequencies were determined by flow cytometric analysis of intracellular cytokine staining for CD69, TNF-α and interferon-γ using RhCMV or overlapping 15 mer peptides corresponding to SIVgag. The percentage of the responding, SIVgag specific T cells within the overall memory subset is shown for each time point. RhCMV-specific responses were measured by adding purified virus.

The mutations may be random or site-directed. For random mutations, mutagenic agents, in particular alkylating mutagenic agents, are diethyl sulfate (des), ethyleneimine (ei), propane sultone, N-methyl-N-nitrosourethane (mnu), N-nitroso-N-methylurea (NMU), N-ethyl-N-nitrosourea (enu), sodium azide may be utilized. Alternatively, the mutations may be induced by means of irradiation, which is for example selected from x-rays, fast neutrons, UV irradiation.

Mutations may be introduced using synthetic oligonucleotides. These oligonucleotides contain nucleotide sequences flanking the desired mutation sites. A suitable method is disclosed in Morinaga et al. (Biotechnology (1984)2, p 646-649). Another method of introducing mutations into enzyme-encoding nucleotide sequences is described in Nelson and Long (Analytical Biochemistry (1989), 180, p 147-151). Instead of site directed mutagenesis, such as described above, one can introduce mutations randomly for instance using a commercial kit such as the GeneMorph PCR mutagenesis kit from Stratagene, or the Diversify PCR random mutagenesis kit from Clontech. EP 0 583 265 refers to methods of optimising PCR based mutagenesis, which can also be combined with the use of mutagenic DNA analogues such as those described in EP 0 866 796. Error prone PCR technologies are suitable for the production of variants of lipid acyl transferases with preferred characteristics.

Antisense techniques as well as direct gene manipulation are known for use in modulating gene expression. The invention thus includes the use of antisense nucleic acids, which may incorporate natural or modified nucleotides, or both, ribozymes, including hammerhead ribozymes, gene knockout such as by homologous recombination, and other techniques for reducing gene expression levels.

RNA interference (RNAi) is a method of post transcriptional gene silencing (PTGS) induced by the direct introduction of double-stranded RNA (dsRNA) and has emerged as a useful tool to knock out expression of specific genes in a variety of organisms. RNAi is described by Fire et al., Nature 391:806-811 (1998). Other methods of PTGS are known and include, for example, introduction of a transgene or virus. Generally, in PTGS, the transcript of the silenced gene is synthesised but does not accumulate because it is rapidly degraded. Methods for PTGS, including RNAi are described, for example, in the Ambion.com world wide web site, in the directory "/hottopics/", in the "rnai" file. Suitable methods for RNAi in vitro are known to those skilled in the art. One such method involves the introduction of siRNA (small interfering RNA). Current models indicate that these 21-23 nucleotide dsRNAs can induce PTGS. Methods for designing effective siRNAs are described, for example, in the Ambion web site described above.

CMV vectors, when used as expression vectors are innately non-pathogenic in the selected subjects such as humans or have been modified to render them non-pathogenic in the selected subjects. For example, replication-defective adenoviruses and alphaviruses are well known and can be used as gene delivery vectors. Without US2-11 all of these vectors (except for CMV which contains US2-11 naturally) elicit vector-specific immunity which prohibits their repeated use.

The present invention also relates to a method of inducing a CD8+ T cell response in a subject, which may comprise (a) administering a CMV vector with at least one cytomegalovirus (CMV) glycoprotein deleted from the CMV vector, wherein the glycoprotein is US11, and wherein the CMV vector contains and expresses at least one heterologous (non-CMV) antigen and (b) administering the vector to the animal or human subject.

The heterologous antigen may be derived from a pathogen. The pathogen may be a viral pathogen and the antigen may be a protein derived from the viral pathogen. Viruses include, but are not limited to Adenovirus, coxsackievirus, hepatitis A virus, poliovirus, rhinovirus, Herpes simplex, type 1, Herpes simplex, type 2, Varicella-zoster virus, Epstein-barr virus, Kaposi's sarcoma herpesvirus, Human cytomegalovirus, Human herpesvirus, type 8, Hepatitis B virus, Hepatitis C virus, yellow fever virus, dengue virus, West Nile virus, Human immunodeficiency virus (HIV), Influenza virus, Measles virus, Mumps virus, Parainfluenza virus, Respiratory syncytial virus, Human metapneumovirus, Human papillomavirus, Rabies virus, Rubella virus, Human bocavirus and Parvovirus B19.

The pathogen may be a bacterial pathogen and the antigen may be a protein derived from the bacterial pathogen. The pathogenic bacteria include, but are not limited to, *Bordetella pertussis, Borrelia burgdorferi, Brucella abortus, Brucella canis, Brucella melitensis, Brucella suis, Campylobacter jejuni, Chlamydia pneumoniae, Chlamydia trachomatis, Chlamydophila psittaci, Clostridium botulinum, Clostridium difficile, Clostridium perfringens, Clostridium tetani, Corynebacterium diphtheriae, Enterococcus faecalis, Enterococcus faecium, Escherichia coli, Francisella tularensis, Haemophilus influenzae, Helicobacter pylori, Legionella pneumophila, Leptospira interrogans, Listeria monocytogenes, Mycobacterium leprae, Mycobacterium tuberculosis, Mycobacterium ulcerans, Mycoplasma pneumoniae, Neisseria gonorrhoeae, Neisseria meningitidis, Pseudomonas aeruginosa, Rickettsia rickettsii, Salmonella typhi, Salmonella typhimurium, Shigella sonnei, Staphylococcus aureus, Staphylococcus epidermidis, Staphylococcus saprophyticus, Streptococcus agalactiae, Streptococcus pneumoniae, Streptococcus pyogenes, Treponema pallidum, Vibrio cholera* and *Yersinia pestis.*

The pathogen may be a parasite and the antigen may be a protein derived from the parasite pathogen. The parasite may be a protozoan organism or disease caused by a protozoan organism such as, but not limited to, Acanthamoeba, Babesiosis, Balantidiasis, Blastocystosis, Coccidia, Dientamoebiasis, Amoebiasis, Giardia, Isosporiasis, Leishmaniasis, Primary amoebic meningoencephalitis (PAM), Malaria, Rhinosporidiosis, Toxoplasmosis—Parasitic pneumonia, Trichomoniasis, Sleeping sickness and Chagas disease. The parasite may be a helminth organism or worm or a disease caused by a helminth organism such as, but not limted to, Ancylostomiasis/Hookworm, Anisakiasis, Roundworm—Parasitic pneumonia, Roundworm—Baylisascariasis, Tapeworm—Tapeworm infection, Clonorchiasis, Dioctophyme renalis infection, Diphyllobothriasis—tapeworm, Guinea worm—Dracunculiasis, Echinococcosis—tapeworm, Pinworm—Enterobiasis, Liver fluke—Fasciolosis, Fasciolopsiasis—intestinal fluke, Gnathostomiasis, Hymenolepiasis, Loa boa filariasis, Calabar swellings, Mansonelliasis, Filariasis, Metagonimiasis—intestinal fluke, River blindness, Chinese Liver Fluke, Paragonimiasis, Lung Fluke, Schistosomiasis—bilharzia, bilharziosis or snail fever (all types), intestinal schistosomiasis, urinary schistosomiasis, Schistosomiasis by Schistosoma japonicum, Asian intestinal schistosomiasis, Sparganosis, Strongyloidiasis—Parasitic pneumonia, Beef tapeworm, Pork tapeworm, Toxocariasis, Trichinosis, Swimmer's itch, Whipworm and Elephantiasis Lymphatic filariasis. The parasite may be an organism or disease caused by an organism such as, but not limited to, parasitic worm, Halzoun Syndrome, Myiasis, Chigoe flea, Human Botfly and Candiru. The parasite may be an ectoparasite or disease caused by an ectoparasite such as, but not limited to, Bedbug, Head louse—Pediculosis, Body louse—Pediculosis, Crab louse—Pediculosis, Demodex—Demodicosis, Scabies, Screwworm and Cochliomyia.

The antigen may be a protein derived from cancer. The cancers, include, but are not limited to, Acute lymphoblastic leukemia; Acute myeloid leukemia; Adrenocortical carcinoma; AIDS-related cancers; AIDS-related lymphoma; Anal cancer; Appendix cancer; Astrocytoma, childhood cerebellar or cerebral; Basal cell carcinoma; Bile duct cancer, extrahepatic; Bladder cancer; Bone cancer, Osteosarcoma/Malignant fibrous histiocytoma; Brainstem glioma; Brain tumor; Brain tumor, cerebellar astrocytoma; Brain tumor, cerebral astrocytoma/malignant glioma; Brain tumor, ependymoma; Brain tumor, medulloblastoma; Brain tumor, supratentorial primitive neuroectodermal tumors; Brain tumor, visual pathway and hypothalamic glioma; Breast cancer; Bronchial adenomas/carcinoids; Burkitt lymphoma; Carcinoid tumor, childhood; Carcinoid tumor, gastrointestinal; Carcinoma of unknown primary; Central nervous system lymphoma, primary; Cerebellar astrocytoma, childhood; Cerebral astrocytoma/Malignant glioma, childhood; Cervical cancer; Childhood cancers; Chronic lymphocytic leukemia; Chronic myelogenous leukemia; Chronic myeloproliferative disorders; Colon Cancer; Cutaneous T-cell lymphoma; Desmoplastic small round cell tumor; Endometrial cancer; Ependymoma; Esophageal cancer; Ewing's sarcoma in the Ewing family of tumors; Extracranial germ cell tumor, Childhood; Extragonadal Germ cell tumor; Extrahepatic bile duct cancer; Eye Cancer, Intraocular melanoma; Eye Cancer, Retinoblastoma; Gallbladder cancer; Gastric (Stomach) cancer; Gastrointestinal Carcinoid Tumor; Gastrointestinal stromal tumor (GIST); Germ cell tumor: extracranial, extragonadal, or ovarian; Gestational trophoblastic tumor; Glioma of the brain stem; Glioma, Childhood Cerebral Astrocytoma; Glioma, Childhood Visual Pathway and Hypothalamic; Gastric carcinoid; Hairy cell leukemia; Head and neck cancer; Heart cancer; Hepatocellular (liver) cancer; Hodgkin lymphoma; Hypopharyngeal cancer; Hypothalamic and visual pathway glioma, childhood; Intraocular Melanoma; Islet Cell Carcinoma (Endocrine Pancreas); Kaposi sarcoma; Kidney cancer (renal cell cancer); Laryngeal Cancer; Leukemias; Leukemia, acute lymphoblastic (also called acute lymphocytic leukemia); Leukemia, acute myeloid (also called acute myelogenous leukemia); Leukemia, chronic lymphocytic (also called chronic lymphocytic leukemia); Leukemia, chronic myelogenous (also called chronic myeloid leukemia); Leukemia, hairy cell; Lip and Oral Cavity Cancer; Liver Cancer (Primary); Lung Cancer, Non-Small Cell; Lung Cancer, Small Cell; Lymphomas; Lymphoma, AIDS-related; Lymphoma, Burkitt; Lymphoma, cutaneous T-Cell; Lymphoma, Hodgkin; Lymphomas, Non-Hodgkin (an old classification of all lymphomas except Hodgkin's); Lymphoma, Primary Central Nervous System; Marcus Whittle, Deadly Disease; Macroglobulinemia, Waldenström; Malignant Fibrous Histiocytoma of Bone/Osteosarcoma; Medulloblastoma, Childhood; Melanoma; Melanoma, Intraocular (Eye); Merkel Cell Carcinoma; Mesothelioma, Adult Malignant; Mesothelioma, Childhood; Metastatic Squamous Neck Cancer with Occult Primary; Mouth Cancer; Multiple Endocrine Neoplasia Syndrome, Childhood; Multiple Myeloma/Plasma Cell Neoplasm; Mycosis Fungoides; Myelodysplastic Syndromes; Myelodysplastic/Myeloproliferative Diseases; Myelogenous Leukemia, Chronic; Myeloid Leukemia, Adult Acute; Myeloid Leukemia, Childhood Acute; Myeloma, Multiple (Cancer of the Bone-Marrow); Myeloproliferative Disorders, Chronic; Nasal cavity and paranasal sinus cancer; Nasopharyngeal carcinoma; Neuroblastoma; Non-Hodgkin lymphoma; Non-small cell lung cancer; Oral Cancer; Oropharyngeal cancer; Osteosarcoma/malignant fibrous histiocytoma of bone; Ovarian cancer; Ovarian epithelial cancer (Surface epithelial-stromal tumor); Ovarian germ cell tumor; Ovarian low malignant potential tumor; Pancreatic cancer; Pancreatic cancer, islet cell; Paranasal sinus and nasal cavity cancer; Parathyroid cancer; Penile cancer; Pharyngeal cancer; Pheochromocytoma; Pineal astrocytoma; Pineal germinoma; Pineoblastoma and supratentorial primitive neuroectodermal tumors, childhood; Pituitary adenoma; Plasma cell neoplasia/Multiple myeloma; Pleuropulmonary blastoma; Primary central nervous system lymphoma; Prostate cancer; Rectal cancer; Renal cell carcinoma (kidney cancer); Renal pelvis and ureter, transitional cell cancer; Retinoblastoma; Rhabdomyosarcoma, childhood; Salivary gland cancer; Sarcoma, Ewing family of tumors; Sarcoma, Kaposi; Sarcoma, soft tissue; Sarcoma, uterine; Sézary syndrome; Skin cancer (nonmelanoma); Skin cancer (melanoma); Skin carcinoma, Merkel cell; Small cell lung cancer; Small intestine cancer; Soft tissue sarcoma; Squamous cell carcinoma—see Skin cancer (nonmelanoma); Squamous neck cancer with occult primary, metastatic; Stomach cancer; Supratentorial primitive neuroectodermal tumor, childhood; T-Cell lymphoma, cutaneous (Mycosis Fungoides and Sézary syndrome); Testicular cancer; Throat cancer; Thymoma, childhood; Thymoma and Thymic carcinoma; Thyroid cancer; Thyroid cancer, childhood; Transitional cell cancer of the renal pelvis and ureter; Trophoblastic tumor, gestational; Unknown primary site, carcinoma of, adult; Unknown primary site, cancer of, childhood; Ureter and renal pelvis, transitional cell cancer; Urethral cancer; Uterine cancer, endometrial; Uterine sarcoma; Vaginal cancer; Visual pathway and hypothalamic glioma, childhood; Vulvar cancer; Waldenström macroglobulinemia and Wilms tumor (kidney cancer).

Accordingly, the invention provides a CMV synthetically modified to contain therein exogenous DNA. The CMV has had US11 deleted therefrom.

The invention further provides a vector for cloning or expression of heterologous DNA which may comprise the recombinant CMV.

The heterologous DNA may encode an expression product which may comprise: an epitope of interest, a biological response modulator, a growth factor, a recognition sequence, a therapeutic gene, or a fusion protein.

An epitope of interest is an antigen or immunologically active fragment thereof from a pathogen or toxin of veterinary or human interest.

An epitope of interest can be an antigen of pathogen or toxin, or from an antigen of a pathogen or toxin, or another antigen or toxin which elicits a response with respect to the pathogen, or from another antigen or toxin which elicits a response with respect to the pathogen.

An epitope of interest can be an antigen of a human pathogen or toxin, or from an antigen of a human pathogen or toxin, or another antigen or toxin which elicits a response with respect to the pathogen, or from another antigen or toxin which elicits a response with respect to the pathogen, such as, for instance: a Morbillivirus antigen, e.g., a measles virus antigen such as HA or F; a rabies glycoprotein, e.g., rabies virus glycoprotein G; an influenza antigen, e.g., influenza virus HA or N; a Herpesvirus antigen, e.g., a glycoprotein of a herpes simplex virus (HSV), a human cytomegalovirus (HCMV), Epstein-Barr; a flavivirus antigen, a JEV, Yellow Fever virus or Dengue virus antigen; a Hepatitis virus antigen, e.g., HBsAg; an immunodeficiency virus antigen, e.g., an HIV antigen such as gp120, gp160; a Hantaan virus antigen; a *C. tetani* antigen; a mumps antigen; a pneumococcal antigen, e.g., PspA; a *Borrelia* antigen, e.g., OspA, OspB, OspC of *Borrelia* associated with Lyme disease such as *Borrelia burgdorferi*, *Borrelia atzelii* and *Borrelia garinii*; a chicken pox (varicella zoster) antigen; or a *Plasmodium* antigen.

The epitope of interest may be derived from an antigen of an immunodeficiency virus such as HIV or SIV. However, the epitope of interest can be an antigen of any veterinary or human pathogen or from any antigen of any veterinary or human pathogen.

Since the heterologous DNA can encode a growth factor or therapeutic gene, the recombinant CMV can be used in gene therapy. Gene therapy involves transferring genetic information; and, with respect to gene therapy and immunotherapy, reference is made to U.S. Pat. No. 5,252,479, which is incorporated herein by reference, together with the documents cited in it and on its face, and to WO 94/16716 and U.S. application Ser. No. 08/184,009, filed Jan. 19, 1994, each of which is also incorporated herein by reference, together with the documents cited therein. The growth factor or therapeutic gene, for example, can encode a disease-fighting protein, a molecule for treating cancer, a tumor suppressor, a cytokine, a tumor associated antigen, or interferon; and, the growth factor or therapeutic gene can, for example, be selected from the group consisting of a gene encoding alpha-globin, beta-globin, gamma-globin, granulocyte macrophage-colony stimulating factor, tumor necrosis factor, an interleukin, macrophage colony stimulating factor, granulocyte colony stimulating factor, erythropoietin, mast cell growth factor, tumor suppressor p53, retinoblastoma, interferon, melanoma associated antigen or B7.

The invention still further provides an immunogenic, immunological or vaccine composition containing the recombinant CMV virus or vector, and a pharmaceutically acceptable carrier or diluent. An immunological composition containing the recombinant CMV virus or vector (or an expression product thereof) elicits an immunological response—local or systemic. The response can, but need not be, protective. An immunogenic composition containing the recombinant CMV virus or vector (or an expression product thereof) likewise elicits a local or systemic immunological response which can, but need not be, protective. A vaccine composition elicits a local or systemic protective response. Accordingly, the terms "immunological composition" and "immunogenic composition" include a "vaccine composition" (as the two former terms can be protective compositions).

The invention therefore also provides a method of inducing an immunological response in a host vertebrate which may comprise administering to the host an immunogenic, immunological or vaccine composition which may comprise the recombinant CMV virus or vector and a pharmaceutically acceptable carrier or diluent. For purposes of this specification, the term "subject" includes all animals and humans, while "animal" includes all vertebrate species, except humans; and "vertebrate" includes all vertebrates, including animals (as "animal" is used herein) and humans. And, of course, a subset of "animal" is "mammal", which for purposes of this specification includes all mammals, except humans.

The invention even further provides a therapeutic composition containing the recombinant CMV virus or vector and a pharmaceutically acceptable carrier or diluent. The therapeutic composition is useful in the gene therapy and immunotherapy embodiments of the invention, e.g., in a method for transferring genetic information to an animal or human in need of such which may comprise administering to the host the composition; and, the invention accordingly includes methods for transferring genetic information.

In yet another embodiment, the invention provides a method of expressing a protein or gene product or an expression product which may comprise infecting or transfecting a cell in vitro with a recombinant CMV virus or vector of the invention and optionally extracting, purifying or isolating the protein, gene product or expression product or DNA from the cell. And, the invention provides a method for cloning or replicating a heterologous DNA sequence which may comprise infecting or transfecting a cell in vitro or in vivo with a recombinant CMV virus or vector of the invention and optionallly extracting, purifying or isolating the DNA from the cell or progeny virus.

The invention in another aspect provides a method for preparing the recombinant CMV virus or vector of the invention which may comprise inserting the exogenous DNA into a non-essential region of the CMV genome.

The method can further comprise deleting a non-essential region from the CMV genome, preferably prior to inserting the exogenous DNA.

The method can comprise in vivo recombination. Thus, the method can comprise transfecting a cell with CMV DNA in a cell-compatible medium in the presence of donor DNA which may comprise the exogenous DNA flanked by DNA sequences homologous with portions of the CMV genome, whereby the exogenous DNA is introduced into the genome of the CMV, and optionally then recovering CMV modified by the in vivo recombination.

The method can also comprise cleaving CMV DNA to obtain cleaved CMV DNA, ligating the exogenous DNA to the cleaved CMV DNA to obtain hybrid CMV-exogenous DNA, tranfecting a cell with the hybrid CMV-exogenous DNA, and optionally then recovering CMV modified by the presence of the exogenous DNA.

Since in vivo recombination is comprehended, the invention accordingly also provides a plasmid which may comprise donor DNA not naturally occurring in CMV encoding a polypeptide foreign to CMV, the donor DNA is within a segment of CMV DNA which would otherwise be co-linear with a non-essential region of the CMV genome such that DNA from a non-essential region of CMV is flanking the donor DNA.

The exogenous DNA can be inserted into CMV to generate the recombinant CMV in any orientation which yields stable integration of that DNA, and expression thereof, when desired.

The exogenous DNA in the recombinant CMV virus or vector of the invention can include a promoter. The promoter can be from a herpes virus. For instance, the promoter can be a cytomegalovirus (CMV) promoter, such as a human CMV (HCMV) or murine CMV promoter. The promoter can also be a non-viral promoter such as the EFla promoter.

The promoter may be a truncated transcriptionally active promoter which may comprise a region transactivated with a transactivating protein provided by the virus and the minimal promoter region of the full-length promoter from which the truncated transcriptionally active promoter is derived. For purposes of this specification, a "promoter" is composed of an association of DNA sequences corresponding to the minimal promoter and upstream regulatory sequences; a "minimal promoter" is composed of the CAP site plus TATA box (minimum sequences for basic level of transcription; unregulated level of transcription); and, "upstream regulatory sequences" are composed of the upstream element(s) and enhancer sequence(s). Further, the term "truncated" indicates that the full-length promoter is not completely present, i.e., that some portion of the full-length promoter has been removed. And, the truncated promoter can be derived from a herpesvirus such as MCMV or HCMV, e.g., HCMV-IE or MCMV-IE.

Like the aforementioned promoter, the inventive promoter can be a herpesvirus, e.g., a MCMV or HCMV such as MCMV-IE or HCMV-IE promoter; and, there can be up to a 40% and even up to a 90% reduction in size, from a full-length promoter, based upon base pairs. The promoter can also be a modified non-viral promoter.

The invention thus also provides an expression cassette for insertion into a recombinant virus or plasmid which may comprise the truncated transcriptionally active promoter. The expression cassette can further include a functional truncated polyadenylation signal; for instance an SV40 polyadenylation signal which is truncated, yet functional. Considering that nature provided a larger signal, it is indeed surprising that a truncated polyadenylation signal is functional; and, a truncated polyadenylation signal addresses the insert size limit problems of recombinant viruses such as CMV. The expression cassette can also include exogenous or heterologous DNA with respect to the virus or system into which it is inserted; and that DNA can be exogenous or heterologous DNA as described herein.

In a more specific aspect, the present invention encompasses CMV, recombinants which may comprise viral or non-viral promoters, preferably a truncated promoter therefrom. The invention further comprehends antibodies elicited by the inventive compositions and/or recombinants and uses for such antibodies. The antibodies, or the product (epitopes of interest) which elicited them, or monoclonal antibodies from the antibodies, can be used in binding assays, tests or kits to determine the presence or absence of an antigen or antibody.

Flanking DNA used in the invention can be from the site of insertion or a portion of the genome adjacent thereto (wherein "adjacent" includes contiguous sequences, e.g., codon or codons, as well as up to as many sequences, e.g., codon or codons, before there is an intervening insertion site).

The exogenous or heterologous DNA (or DNA foreign to CMV, or DNA not naturally occurring in CMV) can be DNA encoding any of the aforementioned epitopes of interest, as listed above. The exogenous DNA can include a marker, e.g., a color or light marker. The exogenous DNA can also code for a product which would be detrimental to an insect host such that the expression product can be a pesticide or insecticide. The exogenous DNA can also code for an anti-fungal polypeptide; and, for information on such a polypeptide and DNA therefor, reference is made to U.S. Pat. No. 5,421,839 and the documents cited therein, incorporated herein by reference.

The heterologous or exogenous DNA in recombinants of the invention preferably encodes an expression product which may comprise: an epitope of interest, a biological response modulator, a growth factor, a recognition sequence, a therapeutic gene, or a fusion protein. With respect to these terms, reference is made to the following discussion, and generally to Kendrew, THE ENCYCLOPEDIA OF MOLECULAR BIOLOGY (Blackwell Science Ltd 1995) and Sambrook, Fritsch, Maniatis, Molecular Cloning, A LABORATORY MANUAL (2d Edition, Cold Spring Harbor Laboratory Press, 1989).

As to antigens for use in vaccine or immunological compositions, see also Stedman's Medical Dictionary (24th edition, 1982), e.g., definition of vaccine (for a list of antigens used in vaccine formulations; such antigens or epitopes of interest from those antigens can be used in the invention, as either an expression product of the inventive recombinant virus, or in a multivalent composition containing an inventive recombinant virus or an expression product therefrom).

As to epitopes of interest, one skilled in the art can determine an epitope or immunodominant region of a peptide or polypeptide and ergo the coding DNA therefor from the knowledge of the amino acid and corresponding DNA sequences of the peptide or polypeptide, as well as from the nature of particular amino acids (e.g., size, charge, etc.) and the codon dictionary, without undue experimentation.

A general method for determining which portions of a protein to use in an immunological composition focuses on the size and sequence of the antigen of interest. "In general, large proteins, because they have more potential determinants are better antigens than small ones. The more foreign an antigen, that is the less similar to self configurations which induce tolerance, the more effective it is in provoking an immune response." Ivan Roitt, Essential Immunology, 1988.

As to size: the skilled artisan can maximize the size of the protein encoded by the DNA sequence to be inserted into the viral vector (keeping in mind the packaging limitations of the vector). To minimize the DNA inserted while maximizing the size of the protein expressed, the DNA sequence can exclude introns (regions of a gene which are transcribed but which are subsequently excised from the primary RNA transcript).

At a minimum, the DNA sequence can code for a peptide at least 8 or 9 amino acids long. This is the minimum length that a peptide needs to be in order to stimulate a CD8+ T cell response (which recognizes virus infected cells or cancerous cells). A minimum peptide length of 13 to 25 amino acids is useful to stimulate a CD4+ T cell response (which recognizes special antigen presenting cells which have engulfed the pathogen). See Kendrew, supra. However, as these are minimum lengths, these peptides are likely to generate an immunological response, i.e., an antibody or T cell response; but, for a protective response (as from a vaccine composition), a longer peptide is preferred.

Figure 2:
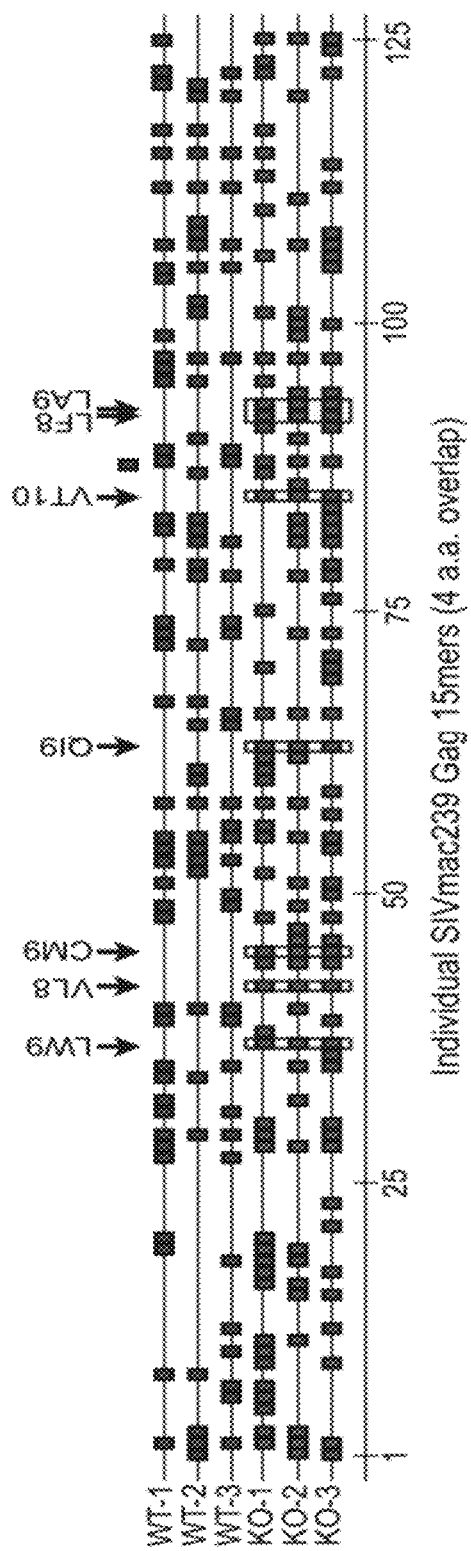
FIG. 2 depicts a chart depicting the recognition of individual, consecutive gag 15 mer peptides by 3 each Mamu A*01+, CMV-naïve RM vaccinated with wt vs. US2-11 knock-out (KO) RhCMV/gag vectors. Note that whereas both wt and KO vectors elicit broad CD8+ T cell gag epitope recognition, only the KO vector-elicited responses include recognition of peptides containing conventional immunodominant epitopes (yellow rectangles; epitopes designated at top).

With respect to the sequence, the DNA sequence preferably encodes at least regions of the peptide that generate an antibody response or a T cell response. One method to determine T and B cell epitopes involves epitope mapping. The protein of interest "is fragmented into overlapping peptides with proteolytic enzymes or overlapping peptides are generated by oligo-peptide synthesis. The individual peptides are then tested for their ability to bind to an antibody elicited by the native protein or to induce T cell or B cell activation. This approach has been particularly useful in mapping T-cell epitopes since the T cell recognizes short linear peptides complexed with MHC molecules (see FIG. 2). The method is less effective for determining B-cell epitopes" since B cell epitopes are often not linear amino acid sequences but rather result from the tertiary structure of the folded three dimensional protein. Janis Kuby, Immunology, (1992) pp. 79-80.

Another method of determining an epitope of interest is to choose the regions of the protein that are hydrophilic. Hydrophilic residues are often on the surface of the protein and are therefore often the regions of the protein which are accessible to the antibody. Janis Kuby, Immunology, (1992) p. 81.

Yet another method for determining an epitope of interest is to perform an X-ray crystallographic analysis of the antigen (full length)-antibody complex. Janis Kuby, Immunology, (1992) p. 80.

Still another method for choosing an epitope of interest which can generate a T cell response is to identify from the protein sequence potential HLA anchor binding motifs which are peptide sequences which are known to be likely to bind to the MHC molecule.

The peptide which is a putative epitope of interest, to generate a T cell response, should be presented in a MHC complex. The peptide preferably contains appropriate anchor motifs for binding to the MHC molecules, and should bind with high enough affinity to generate an immune response. Factors which can be considered are: the HLA type of the patient (vertebrate, animal or human) expected to be immunized, the sequence of the protein, the presence of appropriate anchor motifs and the occurrence of the peptide sequence in other vital cells.

An immune response is generated, in general, as follows: T cells recognize proteins only when the protein has been cleaved into smaller peptides and is presented in a complex called the "major histocompatability complex (MHC)" located on another cell's surface. There are two classes of MHC complexes—class I and class II, and each class is made up of many different alleles. Different species, and individual subjects have different types of MHC complex alleles; they are said to have a different HLA type.

Class I MHC complexes are found on virtually every cell and present peptides from proteins produced inside the cell. Thus, Class I MHC complexes are useful for killing cells which when infected by viruses or which have become cancerous and as the result of expression of an oncogene. T cells which have a protein called CD8 on their surface, bind to the MHC class I cells and secrete lymphokines. The lymphokines stimulate a response; cells arrive and kill the viral infected cell.

Class II MHC complexes are found only on antigen-presenting cells and are used to present peptides from circulating pathogens which have been endocytosed by the antigen-presenting cells. T cells which have a protein called CD4 bind to the MHC class II cells and kill the cell by exocytosis of lytic granules.

Some guidelines in determining whether a protein is an epitope of interest which will stimulate a T cell response, include: Peptide length—the peptide should be at least 8 or 9 amino acids long to fit into the MHC class I complex and at least 13-25 amino acids long to fit into a class II MCH complex. This length is a minimum for the peptide to bind to the MHC complex. It is preferred for the peptides to be longer than these lengths because cells may cut the expressed peptides. The peptide should contain an appropriate anchor motif which will enable it to bind to the various class I or class II molecules with high enough specificity to generate an immune response (See Bocchia, M. et al., Specific Binding of Leukemia Oncogene Fusion Protein Peptides to HLA Class I Molecules, Blood 85:2680-2684; Englehard, V H, Structure of peptides associated with class I and class II MHC molecules, Ann. Rev. Immunol. 12:181 (1994)). This can be done, without undue experimentation, by comparing the sequence of the protein of interest with published structures of peptides associated with the MHC molecules. Protein epitopes recognized by T cell receptors are peptides generated by enzymatic degradation of the protein molecule and are presented on the cell surface in association with class I or class II MHC molecules.

Further, the skilled artisan can ascertain an epitope of interest by comparing the protein sequence with sequences listed in the protein data base. Regions of the protein which share little or no homology are better choices for being an epitope of that protein and are therefore useful in a vaccine or immunological composition. Regions which share great homology with widely found sequences present in vital cells should be avoided.

Even further, another method is simply to generate or express portions of a protein of interest, generate monoclonal antibodies to those portions of the protein of interest, and then ascertain whether those antibodies inhibit growth in vitro of the pathogen from which the protein was derived. The skilled artisan can use the other guidelines set forth in this disclosure and in the art for generating or expressing portions of a protein of interest for analysis as to whether antibodies thereto inhibit growth in vitro. For example, the skilled artisan can generate portions of a protein of interest by: selecting 8 to 9 or 13 to 25 amino acid length portions of the protein, selecting hydrophilic regions, selecting portions shown to bind from X-ray data of the antigen (full length)-antibody complex, selecting regions which differ in sequence from other proteins, selecting potential HLA anchor binding motifs, or any combination of these methods or other methods known in the art.

Epitopes recognized by antibodies are expressed on the surface of a protein. To determine the regions of a protein most likely to stimulate an antibody response one skilled in the art can preferably perform an epitope map, using the general methods described above, or other mapping methods known in the art.

As can be seen from the foregoing, without undue experimentation, from this disclosure and the knowledge in the art, the skilled artisan can ascertain the amino acid and corresponding DNA sequence of an epitope of interest for obtaining a T cell, B cell and/or antibody response. In addition, reference is made to Gefter et al., U.S. Pat. No. 5,019,384, issued May 28, 1991, and the documents it cites, incorporated herein by reference (Note especially the "Relevant Literature" section of this patent, and column 13 of this patent which discloses that: "A large number of epitopes have been defined for a wide variety of organisms of interest. Of particular interest are those epitopes to which neutralizing antibodies are directed.")

With respect to expression of a biological response modulator, reference is made to Wohlstadter, "Selection Methods," WO 93/19170, published Sep. 30, 1993, and the documents cited therein, incorporated herein by reference.

For instance, a biological response modulator modulates biological activity; for instance, a biological response modulator is a modulatory component such as a high molecular weight protein associated with non-NMDA excitatory amino acid receptors and which allosterically regulates affinity of AMPA binding (See Kendrew, supra). The recombinant of the present invention can express such a high molecular weight protein.

More generally, nature has provided a number of precedents of biological response modulators. Modulation of activity may be carried out through mechanisms as complicated and intricate as allosteric induced quaternary change to simple presence/absence, e.g., expression/degradation, systems. Indeed, the repression/activation of expression of many biological molecules is itself mediated by molecules whose activities are capable of being modulated through a variety of mechanisms.

Table 2 of Neidhardt et al., Physiology of the Bacterial Cell (Sinauer Associates Inc., Publishers, 1990), at page 73, lists chemical modifications to bacterial proteins. As is noted in that table, some modifications are involved in proper assembly and other modifications are not, but in either case such modifications are capable of causing modulation of function. From that table, analogous chemical modulations for proteins of other cells can be determined, without undue experimentation.

In some instances modulation of biological functions may be mediated simply through the proper/improper localization of a molecule. Molecules may function to provide a growth advantage or disadvantage only if they are targeted to a particular location. For example, a molecule may be typically not taken up or used by a cell, as a function of that molecule being first degraded by the cell by secretion of an enzyme for that degradation. Thus, production of the enzyme by a recombinant can regulate use or uptake of the molecule by a cell. Likewise, the recombinant can express a molecule which binds to the enzyme necessary for uptake or use of a molecule, thereby similarly regulating its uptake or use.

Localization targeting of proteins carried out through cleavage of signal peptides which is another type of modulation or regulation. In this case, a specific endoprotease catalytic activity can be expressed by the recombinant.

Other examples of mechanisms through which modulation of function may occur are RNA virus poly-proteins, allosteric effects, and general covalent and non-covalent steric hindrance. HIV is a well studied example of an RNA virus which expresses non-functional poly-protein constructs. In HIV "the gag, pol, and env poly-proteins are processed to yield, respectively, the viral structural proteins p17, p24, and p15—reverse transcriptase and integrase—and the two envelope proteins gp41 and gp120" (Kohl et al., PNAS USA 85:4686-90 (1988)). The proper cleavage of the poly-proteins is crucial for replication of the virus, and virions carrying inactive mutant HIV protease are non-infectious. This is another example of the fusion of proteins down-modulating their activity. Thus, it is possible to construct recombinant viruses which express molecules which interfere with endoproteases, or which provide endoproteases, for inhibiting or enhancing the natural expression of certain proteins (by interfering with or enhancing cleavage).

The functional usefulness of enzymes may also be modulated by altering their capability of catalyzing a reaction. Illustrative examples of modulated molecules are zymogens, formation/disassociation of multi-subunit functional complexes, RNA virus poly-protein chains, allosteric interactions, general steric hindrance (covalent and non-covalent) and a variety of chemical modifications such as phosphorylation, methylation, acetylation, adenylation, and uridenylation (see Table 1 of Neidhardt, supra, at page 315 and Table 2 at page 73).

Zymogens are examples of naturally occurring protein fusions which cause modulation of enzymatic activity. Zymogens are one class of proteins which are converted into their active state through limited proteolysis. See Table 3 of Reich, Proteases and Biological Control, Vol. 2, (1975) at page 54). Nature has developed a mechanism of down-modulating the activity of certain enzymes, such as trypsin, by expressing these enzymes with additional "leader" peptide sequences at their amino termini. With the extra peptide sequence the enzyme is in the inactive zymogen state. Upon cleavage of this sequence the zymogen is converted to its enzymatically active state. The overall reaction rates of the zymogen are "about $10^5$-$10^6$ times lower than those of the corresponding enzyme" (See Table 3 of Reich, supra at page 54).

It is therefore possible to down-modulate the function of certain enzymes simply by the addition of a peptide sequence to one of its termini. For example, with knowledge of this property, a recombinant can express peptide sequences containing additional amino acids at one or both termini.

The formation or disassociation of multi-subunit enzymes is another way through which modulation may occur. Different mechanisms may be responsible for the modulation of activity upon formation or disassociation of multi-subunit enzymes.

Therefore, sterically hindering the proper specific subunit interactions will down-modulate the catalytic activity. And accordingly, the recombinant of the invention can express a molecule which sterically hinders a naturally occurring enzyme or enzyme complex, so as to modulate biological functions.

Certain enzyme inhibitors afford good examples of down-modulation through covalent steric hindrance or modification. Suicide substrates which irreversibly bind to the active site of an enzyme at a catalytically important amino acid in the active site are examples of covalent modifications which sterically block the enzymatic active site. An example of a suicide substrate is TPCK for chymotrypsin (Fritsch, Enzyme Structure and Mechanism, 2d ed; Freeman & Co. Publishers, 1984). This type of modulation is possible by the recombinant expressing a suitable suicide substrate, to thereby modulate biological responses (e.g., by limiting enzyme activity).

There are also examples of non-covalent steric hindrance including many repressor molecules. The recombinant can express repressor molecules which are capable of sterically hindering and thus down-modulating the function of a DNA sequence by preventing particular DNA-RNA polymerase interactions.

Allosteric effects are another way through which modulation is carried out in some biological systems. Aspartate transcarbamoylase is a well characterized allosteric enzyme. Interacting with the catalytic subunits are regulatory domains. Upon binding to CTP or UTP the regulatory subunits are capable of inducing a quaternary structural change in the holoenzyme causing down-modulation of catalytic activity. In contrast, binding of ATP to the regulatory subunits is capable of causing up-modulation of catalytic activity (Fritsch, supra). Using methods of the invention, molecules can be expressed which are capable of binding and causing modulatory quaternary or tertiary changes.

In addition, a variety of chemical modifications, e.g., phosphorylation, methylation, acetylation, adenylation, and uridenylation may be carried out so as to modulate function. It is known that modifications such as these play important roles in the regulation of many important cellular components. Table 2 of Neidhardt, supra, at page 73, lists different bacterial enzymes which undergo such modifications. From that list, one skilled in the art can ascertain other enzymes of other systems which undergo the same or similar modifications, without undue experimentation. In addition, many proteins which are implicated in human disease also undergo such chemical modifications. For example, many oncogenes have been found to be modified by phosphorylation or to modify other proteins through phosphorylation or dephosphorylation. Therefore, the ability afforded by the invention to express modulators which can modify or alter function, e.g., phosphorylation, is of importance.

From the foregoing, the skilled artisan can use the present invention to express a biological response modulator, without any undue experimentation.

With respect to expression of fusion proteins by inventive recombinants, reference is made to Sambrook, Fritsch, Maniatis, Molecular Cloning, A LABORATORY MANUAL (2d Edition, Cold Spring Harbor Laboratory Press, 1989) (especially Volume 3), and Kendrew, supra, incorporated herein by reference. The teachings of Sambrook et al., can be suitably modified, without undue experimentation, from this disclosure, for the skilled artisan to generate recombinants expressing fusion proteins.

With regard to gene therapy and immunotherapy, reference is made to U.S. Pat. Nos. 4,690,915 and 5,252,479, which are incorporated herein by reference, together with the documents cited therein it and on their face, and to WO 94/16716 and U.S. application Ser. No. 08/184,009, filed Jan. 19, 1994, each of which is also incorporated herein by reference, together with the documents cited therein.

A growth factor can be defined as multifunctional, locally acting intercellular signaling peptides which control both ontogeny and maintenance of tissue and function (see Kendrew, especially at page 455 et seq.).

The growth factor or therapeutic gene, for example, can encode a disease-fighting protein, a molecule for treating cancer, a tumor suppressor, a cytokine, a tumor associated antigen, or interferon; and, the growth factor or therapeutic gene can, for example, be selected from the group consisting of a gene encoding alpha-globin, beta-globin, gamma-globin, granulocyte macrophage-colony stimulating factor, tumor necrosis factor, an interleukin (e.g., an interleukin selected from interleukins 1 to 14, or 1 to 11, or any combination thereof), macrophage colony stimulating factor, granulocyte colony stimulating factor, erythropoietin, mast cell growth factor, tumor suppressor p53, retinoblastoma, interferon, melanoma associated antigen or B7. U.S. Pat. No. 5,252,479 provides a list of proteins which can be expressed in an adenovirus system for gene therapy, and the skilled artisan is directed to that disclosure. WO 94/16716 and U.S. application Ser. No. 08/184,009, filed Jan. 19, 1994, provide genes for cytokines and tumor associated antigens and immunotherapy methods, including ex vivo methods, and the skilled artisan is directed to those disclosures.

Thus, one skilled in the art can create recombinants expressing a growth factor or therapeutic gene and use the recombinants, from this disclosure and the knowledge in the art, without undue experimentation.

Moreover, from the foregoing and the knowledge in the art, no undue experimentation is required for the skilled artisan to construct an inventive recombinant which expresses an epitope of interest, a biological response modulator, a growth factor, a recognition sequence, a therapeutic gene, or a fusion protein; or for the skilled artisan to use such a recombinant.

It is noted that the exogenous or heterologous DNA can itself include a promoter for driving expression in the recombinant CMV, or the exogenous DNA can simply be coding DNA and appropriately placed downstream from a CMV-endogenous promoter to drive expression. Further, multiple copies of coding DNA or use of a strong or early promoter or early and late promoter, or any combination thereof, can be done so as to amplify or increase expression. Thus, the exogenous or heterologous DNA can be suitably positioned with respect to a CMV-endogenous promoter, or those promoters can be translocated to be inserted at another location, with the exogenous or heterologous DNA. The coding DNA can be DNA coding for more than one protein so as to have expression of more than one product from the recombinant CMV.

The expression products can be antigens, immunogens or epitopes of interest; and therefore, the invention further relates to immunological, antigenic or vaccine compositions containing the expression products. Further, since the CMV vector, in certain instances, can be administered directly to a suitable host, the invention relates to compositions containing the CMV vector. Additionally, since the expression product can be isolated from the CMV vector in vitro or from cells infected or transfected by the CMV vector in vitro, the invention relates to methods for expressing a product, e.g., which may comprise inserting the exogenous DNA into a CMV as a vector, e.g., by restriction/ligation or by recombination followed by infection or transfection of suitable cells in vitro with a recombinant CMV, and optionally extracting, purifying or isolating the expression product from the cells. Any suitable extraction, purification or isolation techniques can be employed.

In particular, after infecting cells with the recombinant CMV, the protein(s) from the expression of the exogenous DNA are collected by known techniques such as chromatography (see Robbins, EPA 0162738A1; Panicali, EPA 0261940A2); Richardson, supra; Smith et al., supra; Pennock et al., supra; EP Patent Publication No. 0265785). The collected protein(s) can then be employed in a vaccine, antigenic or immunological composition which also contains a suitable carrier.

Thus, the recombinant CMV can be used to prepare proteins such as antigens, immunogens, epitopes of interest, etc. which can be further used in immunological, antigenic or vaccine compositions. It is noted that a recombinant CMV expressing a product detrimental to growth or development of insects can be used to prepare an insecticide, and a recombinant CMV expressing a product detrimental to growth of plants can be used to prepare a herbicide (by isolating the expression product and admixing it with an insecticidally or herbicidally acceptable carrier or diluent) and a recombinant CMV expressing an anti-fungal polypeptide can be used to prepare an anti-fungal preparation (by isolating the expression product and admixing it with a suitable carrier or diluent).

As the expression products can provide an antigenic, immunological or protective (vaccine) response, the invention further relates to products therefrom; namely, antibodies and uses thereof. More in particular, the expression products can elicit antibodies. The antibodies can be formed into monoclonal antibodies; and, the antibodies or expression products can be used in kits, assays, tests, and the like involving binding, so that the invention relates to these uses too. Additionally, since the recombinants of the invention can be used to replicate DNA, the invention relates to recombinant CMV as a vector and methods for replicating DNA by infecting or transfecting cells with the recombinant and harvesting DNA therefrom. The resultant DNA can be used as probes or primers or for amplification.

The administration procedure for recombinant CMV or expression product thereof, compositions of the invention such as immunological, antigenic or vaccine compositions or therapeutic compositions can be via a parenteral route (intradermal, intramuscular, or subcutaneous). Such an administration enables a systemic immune response. The administration can be via a mucosal route, e.g., oral, nasal, genital, etc. Such an administration enables a local immune response.

More generally, the inventive antigenic, immunological or vaccine compositions or therapeutic compositions (compositions containing the CMV recombinants of the invention or expression products) can be prepared in accordance with standard techniques well known to those skilled in the pharmaceutical arts. Such compositions can be administered in dosages and by techniques well known to those skilled in the medical arts taking into consideration such factors as the breed or species, age, sex, weight, and condition of the particular patient, and the route of administration. The compositions can be administered alone, or can be co-administered or sequentially administered with other compositions of the invention or with other immunological, antigenic or vaccine or therapeutic compositions. Such other compositions can include purified native antigens or epitopes or antigens or epitopes from the expression by a recombinant CMV or another vector system; and are administered taking into account the aforementioned factors.

Examples of compositions of the invention include liquid preparations for orifice, e.g., oral, nasal, anal, genital, e.g., vaginal, etc., administration such as suspensions, syrups or elixirs; and, preparations for parenteral, subcutaneous, intradermal, intramuscular or intravenous administration (e.g., injectable administration) such as sterile suspensions or emulsions. In such compositions the recombinant may be in admixture with a suitable carrier, diluent, or excipient such as sterile water, physiological saline, glucose or the like.

Antigenic, immunological or vaccine compositions typically can contain an adjuvant and an amount of the recombinant CMV or expression product to elicit the desired response. In human applications, alum (aluminum phosphate or aluminum hydroxide) is a typical adjuvant. Saponin and its purified component Quil A, Freund's complete adjuvant and other adjuvants used in research and veterinary applications have toxicities which limit their potential use in human vaccines. Chemically defined preparations such as muramyl dipeptide, monophosphoryl lipid A, phospholipid conjugates such as those described by Goodman-Snitkoff et al., J. Immunol. 147:410-415 (1991) and incorporated by reference herein, encapsulation of the protein within a proteoliposome as described by Miller et al., J. Exp. Med. 176:1739-1744 (1992) and incorporated by reference herein, and encapsulation of the protein in lipid vesicles such as Novasome lipid vesicles (Micro Vescular Systems, Inc., Nashua, N.H.) can also be used.

The composition may be packaged in a single dosage form for immunization by parenteral (i.e., intramuscular, intradermal or subcutaneous) administration or orifice administration, e.g., perlingual (i.e., oral), intragastric, mucosal including intraoral, intraanal, intravaginal, and the like administration. And again, the effective dosage and route of administration are determined by the nature of the composition, by the nature of the expression product, by expression level if recombinant CMV is directly used, and by known factors, such as breed or species, age, sex, weight, condition and nature of host, as well as $LD_{50}$ and other screening procedures which are known and do not require undue experimentation. Dosages of expressed product can range from a few to a few hundred micrograms, e.g., 5 to 500 µg. The inventive recombinant can be administered in any suitable amount to achieve expression at these dosage levels. The vaccinal CMV is administered in an amount of at least $10^2$ pfu; thus, the inventive recombinant can be administered in at least this amount; or in a range from about $10^2$ pfu to about $10^7$ pfu. Other suitable carriers or diluents can be water or a buffered saline, with or without a preservative. The expression product or recombinant CMV may be lyophilized for resuspension at the time of administration or can be in solution.

The carrier may also be a polymeric delayed release system. Synthetic polymers are particularly useful in the formulation of a composition having controlled release. An early example of this was the polymerization of methyl methacrylate into spheres having diameters less than one micron to form so-called nano particles, reported by Kreuter, J., Microcapsules and Nanoparticles in Medicine and Pharmacology, M. Donbrow (Ed). CRC Press, pp. 125-148.

Microencapsulation has been applied to the injection of microencapsulated pharmaceuticals to give a controlled release. A number of factors contribute to the selection of a particular polymer for microencapsulation. The reproducibility of polymer synthesis and the microencapsulation process, the cost of the microencapsulation materials and process, the toxicological profile, the requirements for variable release kinetics and the physicochemical compatibility of the polymer and the antigens are all factors that must be considered. Examples of useful polymers are polycarbonates, polyesters, polyurethanes, polyorthoesters and polyamides, particularly those that are biodegradable.

A frequent choice of a carrier for pharmaceuticals and more recently for antigens is poly (d,1-lactide-co-glycolide) (PLGA). This is a biodegradable polyester that has a long history of medical use in erodible sutures, bone plates and other temporary prostheses where it has not exhibited any toxicity. A wide variety of pharmaceuticals including peptides and antigens have been formulated into PLGA microcapsules. A body of data has accumulated on the adaption of PLGA for the controlled release of antigen, for example, as reviewed by Eldridge, J. H., et al., Current Topics in Microbiology and Immunology. 1989, 146:59-66. The entrapment of antigens in PLGA microspheres of 1 to 10 microns in diameter has been shown to have a remarkable adjuvant effect when administered orally. The PLGA microencapsulation process uses a phase separation of a water-in-oil emulsion. The compound of interest is prepared as an aqueous solution and the PLGA is dissolved in suitable organic solvents such as methylene chloride and ethyl acetate. These two immiscible solutions are co-emulsified by high-speed stirring. A non-solvent for the polymer is then added, causing precipitation of the polymer around the aqueous droplets to form embryonic microcapsules. The microcapsules are collected, and stabilized with one of an assortment of agents (polyvinyl alcohol (PVA), gelatin, alginates, polyvinylpyrrolidone (PVP), methyl cellulose) and the solvent removed by either drying in vacuo or solvent extraction.

Thus, solid, including solid-containing-liquid, liquid, and gel (including "gel caps") compositions are envisioned.

Additionally, the inventive vectors, e.g., recombinant CMV, and the expression products therefrom can stimulate an immune or antibody response in animals. From those antibodies, by techniques well-known in the art, monoclonal antibodies can be prepared and, those monoclonal antibodies can be employed in well-known antibody binding assays, diagnostic kits or tests to determine the presence or absence of antigen(s) and therefrom the presence or absence of the natural causative agent of the antigen or, to determine whether an immune response to that agent or to the antigen(s) has simply been stimulated.

Monoclonal antibodies are immunoglobulin produced by hybridoma cells. A monoclonal antibody reacts with a single antigenic determinant and provides greater specificity than a conventional, serum-derived antibody. Furthermore, screening a large number of monoclonal antibodies makes it possible to select an individual antibody with desired specificity, avidity and isotype. Hybridoma cell lines provide a constant, inexpensive source of chemically identical antibodies and preparations of such antibodies can be easily standardized. Methods for producing monoclonal antibodies are well known to those of ordinary skill in the art, e.g., Koprowski, H. et al., U.S. Pat. No. 4,196,265, issued Apr. 1, 1989, incorporated herein by reference.

Uses of monoclonal antibodies are known. One such use is in diagnostic methods, e.g., David, G. and Greene, H., U.S. Pat. No. 4,376,110, issued Mar. 8, 1983, incorporated herein by reference.

Monoclonal antibodies have also been used to recover materials by immunoadsorption chromatography, e.g. Milstein, C., 1980, Scientific American 243:66, 70, incorporated herein by reference.

Furthermore, the inventive recombinant CMV or expression products therefrom can be used to stimulate a response in cells in vitro or ex vivo for subsequent reinfusion into a patient. If the patient is seronegative, the reinfusion is to stimulate an immune response, e.g., an immunological or antigenic response such as active immunization. In a seropositive individual, the reinfusion is to stimulate or boost the immune system against a pathogen.

The recombinant CMV of the invention is also useful for generating DNA for probes or for PCR primers which can be used to detect the presence or absence of hybridizable DNA or to amplify DNA, e.g., to detect a pathogen in a sample or for amplifying DNA.

Furthermore, as discussed above, the invention comprehends promoters and expression cassettes which are useful in adenovirus systems, as well as in any viral or cell system which provides a transactivating protein.

The expression cassette of the invention can further include a functional truncated polyadenylation signal; for instance an SV40 polyadenylation signal which is truncated, yet functional. The expression cassette can contain exogenous or heterologous DNA (with respect to the virus or system into which the promoter or expression cassette is being inserted); for instance exogenous or heterologous coding DNA as herein described above, and in the Examples. This DNA can be suitably positioned and operably linked to the promoter for expression. The expression cassette can be inserted in any orientation; preferably the orientation which obtains maximum expression from the system or virus into which the expression cassette is inserted.

While the promoter and expression cassette are specifically exemplified with reference to adenoviruses, the skilled artisan can adapt these embodiments of the invention to other viruses and to plasmids for cells such as eukaryotic cells, without undue experimentation, by simply ascertaining whether the virus, plasmid, cell or system provides the transactivating protein.

As to HCMV promoters, reference is made to U.S. Pat. Nos. 5,168,062 and 5,385,839, incorporated herein by reference. As to transfecting cells with plasmid DNA for expression therefrom, reference is made to Felgner et al. (1994), J. Biol. Chem. 269, 2550-2561, incorporated herein by reference. And, as to direct injection of plasmid DNA as a simple and effective method of vaccination against a variety of infectious diseases (reference is made to Science, 259:1745-49, 1993, incorporated herein by reference). It is therefore within the scope of this invention that the inventive promoter and expression cassette be used in systems other than adenovirus; for example, in plasmids for the direct injection of plasmid DNA.

The protein fragments of the present invention form a further aspect of the invention; and, such compounds may be used in methods of medical treatments, such as for diagnosis, preventing or treating HIV or for eliciting antibodies for diagnosis of HIV, including use in vaccines. Further, such compounds may be used in the preparation of medicaments for such treatments or prevention, or compositions for diagnostic purposes. The compounds may be employed alone or in combination with other treatments, vaccines or preventatives; and, the compounds may be used in the preparation of combination medicaments for such treatments or prevention, or in kits containing the compound and the other treatment or preventative.

In yet another embodiment, the present invention also encompassed the use of the protein fragments of the present invention described herein as immunogens, advantageously as HIV-1 vaccine components.

The terms "protein", "peptide", "polypeptide", and "amino acid sequence" are used interchangeably herein to refer to polymers of amino acid residues of any length. The polymer may be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

As used herein, the terms "antigen" or "immunogen" are used interchangeably to refer to a substance, typically a protein, which is capable of inducing an immune response in a subject. The term also refers to proteins that are immunologically active in the sense that once administered to a subject (either directly or by administering to the subject a nucleotide sequence or vector that encodes the protein) is able to evoke an immune response of the humoral and/or cellular type directed against that protein.

The term "antibody" includes intact molecules as well as fragments thereof, such as Fab, F(ab')2, Fv and scFv which are capable of binding the epitope determinant. These antibody fragments retain some ability to selectively bind with its antigen or receptor and include, for example:

a. Fab, the fragment which contains a monovalent antigen-binding fragment of an antibody molecule, can be produced by digestion of whole antibody with the enzyme papain to yield an intact light chain and a portion of one heavy chain;
b. Fab', the fragment of an antibody molecule, can be obtained by treating whole antibody with pepsin, followed by reduction, to yield an intact light chain and a portion of the heavy chain; two Fab' fragments are obtained per antibody molecule;
c. F(ab')2, the fragment of the antibody that can be obtained by treating whole antibody with the enzyme pepsin without subsequent reduction; F(ab')2 is a dimer of two Fab' fragments held together by two disulfide bonds;
d. scFv, including a genetically engineered fragment containing the variable region of a heavy and a light chain as a fused single chain molecule.

General methods of making these fragments are known in the art. (See for example, Harlow and Lane, Antibodies: A Laboratory Manual, Cold Spring Harbor Laboratory, New York (1988), which is incorporated herein by reference).

A "neutralizing antibody" may inhibit the entry of HIV-1 virus for example SF162 and/or JRCSF with a neutralization index>1.5 or >2.0. Broad and potent neutralizing antibodies may neutralize greater than about 50% of HIV-1 viruses (from diverse clades and different strains within a clade) in a neutralization assay. The inhibitory concentration of the monoclonal antibody may be less than about 25 mg/ml to neutralize about 50% of the input virus in the neutralization assay.

It should be understood that the proteins and the nucleic acids encoding them may differ from the exact sequences illustrated and described herein. Thus, the invention contemplates deletions, additions, truncations, and substitutions to the sequences shown, so long as the sequences function in accordance with the methods of the invention. In this regard, substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids. It is reasonably predictable that an isolated replacement of leucine with isoleucine or valine, or vice versa; an aspartate with a glutamate or vice versa; a threonine with a serine or vice versa; or a similar conservative replacement of an amino acid with a structurally related amino acid, will not have a major effect on the biological activity. Proteins having substantially the same amino acid sequence as the sequences illustrated and described but possessing minor amino acid substitutions that do not substantially affect the immunogenicity of the protein are, therefore, within the scope of the invention.

As used herein the terms "nucleotide sequences" and "nucleic acid sequences" refer to deoxyribonucleic acid (DNA) or ribonucleic acid (RNA) sequences, including, without limitation, messenger RNA (mRNA), DNA/RNA hybrids, or synthetic nucleic acids. The nucleic acid can be single-stranded, or partially or completely double-stranded (duplex). Duplex nucleic acids can be homoduplex or heteroduplex.

As used herein the term "transgene" may be used to refer to "recombinant" nucleotide sequences that may be derived from any of the nucleotide sequences encoding the proteins of the present invention. The term "recombinant" means a nucleotide sequence that has been manipulated "by man" and which does not occur in nature, or is linked to another nucleotide sequence or found in a different arrangement in nature. It is understood that manipulated "by man" means manipulated by some artificial means, including by use of machines, codon optimization, restriction enzymes, etc.

For example, in one embodiment the nucleotide sequences may be mutated such that the activity of the encoded proteins in vivo is abrogated. In another embodiment the nucleotide sequences may be codon optimized, for example the codons may be optimized for human use. In preferred embodiments the nucleotide sequences of the invention are both mutated to abrogate the normal in vivo function of the encoded proteins, and codon optimized for human use. For example, each of the Gag, Pol, Env, Nef, RT, and Int sequences of the invention may be altered in these ways.

As regards codon optimization, the nucleic acid molecules of the invention have a nucleotide sequence that encodes the antigens of the invention and can be designed to employ codons that are used in the genes of the subject in which the antigen is to be produced. Many viruses, including HIV and other lentiviruses, use a large number of rare codons and, by altering these codons to correspond to codons commonly used in the desired subject, enhanced expression of the antigens can be achieved. In a preferred embodiment, the codons used are "humanized" codons, i.e., the codons are those that appear frequently in highly expressed human genes (Andre et al., J. Virol. 72:1497-1503, 1998) instead of those codons that are frequently used by HIV. Such codon usage provides for efficient expression of the transgenic HIV proteins in human cells. Any suitable method of codon optimization may be used. Such methods, and the selection of such methods, are well known to those of skill in the art. In addition, there are several companies that will optimize codons of sequences, such as Geneart (geneart.com). Thus, the nucleotide sequences of the invention can readily be codon optimized.

The invention further encompasses nucleotide sequences encoding functionally and/or antigenically equivalent variants and derivatives of the CMV vectors and the glycoproteins included therein. These functionally equivalent variants, derivatives, and fragments display the ability to retain antigenic activity. For instance, changes in a DNA sequence that do not change the encoded amino acid sequence, as well as those that result in conservative substitutions of amino acid residues, one or a few amino acid deletions or additions, and substitution of amino acid residues by amino acid analogs are those which will not significantly affect properties of the encoded polypeptide. Conservative amino acid substitutions are glycine/alanine; valine/isoleucine/leucine; asparagine/glutamine; aspartic acid/glutamic acid; serine/threonine/methionine; lysine/arginine; and phenylalanine/tyrosine/tryptophan. In one embodiment, the variants have at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% homology or identity to the antigen, epitope, immunogen, peptide or polypeptide of interest.

For the purposes of the present invention, sequence identity or homology is determined by comparing the sequences when aligned so as to maximize overlap and identity while minimizing sequence gaps. In particular, sequence identity may be determined using any of a number of mathematical algorithms. A nonlimiting example of a mathematical algorithm used for comparison of two sequences is the algorithm of Karlin & Altschul, Proc. Natl. Acad. Sci. USA 1990; 87: 2264-2268, modified as in Karlin & Altschul, Proc. Natl. Acad. Sci. USA 1993; 90: 5873-5877.

Another example of a mathematical algorithm used for comparison of sequences is the algorithm of Myers & Miller, CABIOS 1988; 4: 11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson & Lipman, Proc. Natl. Acad. Sci. USA 1988; 85: 2444-2448.

Advantageous for use according to the present invention is the WU-BLAST (Washington University BLAST) version 2.0 software. WU-BLAST version 2.0 executable programs for several UNIX platforms can be downloaded. This program is based on WU-BLAST version 1.4, which in turn is based on the public domain NCBI-BLAST version 1.4 (Altschul & Gish, 1996, Local alignment statistics, Doolittle ed., *Methods in Enzymology* 266: 460-480; Altschul et al., *Journal of Molecular Biology* 1990; 215: 403-410; Gish & States, 1993; *Nature Genetics* 3: 266-272; Karlin & Altschul, 1993; *Proc. Natl. Acad. Sci. USA* 90: 5873-5877; all of which are incorporated by reference herein).

The various recombinant nucleotide sequences and antibodies and/or antigens of the invention are made using standard recombinant DNA and cloning techniques. Such techniques are well known to those of skill in the art. See for example, "Molecular Cloning: A Laboratory Manual", second edition (Sambrook et al. 1989).

The nucleotide sequences of the present invention may be inserted into "vectors." The term "vector" is widely used and understood by those of skill in the art, and as used herein the term "vector" is used consistent with its meaning to those of skill in the art. For example, the term "vector" is commonly used by those skilled in the art to refer to a vehicle that allows or facilitates the transfer of nucleic acid molecules from one environment to another or that allows or facilitates the manipulation of a nucleic acid molecule.

Any vector that allows expression of the viruses of the present invention may be used in accordance with the present invention. In certain embodiments, the viruses of the present invention may be used in vitro (such as using cell-free expression systems) and/or in cultured cells grown in vitro in order to produce the encoded HIV-antigens and/or antibodies which may then be used for various applications such as in the production of proteinaceous vaccines. For such applications, any vector that allows expression of the virus in vitro and/or in cultured cells may be used.

For the exogenous antigens of the present invention to be expressed, the protein coding sequence of the exogenous antigen should be "operably linked" to regulatory or nucleic acid control sequences that direct transcription and translation of the protein. As used herein, a coding sequence and a nucleic acid control sequence or promoter are said to be "operably linked" when they are covalently linked in such a way as to place the expression or transcription and/or translation of the coding sequence under the influence or control of the nucleic acid control sequence. The "nucleic acid control sequence" can be any nucleic acid element, such as, but not limited to promoters, enhancers, IRES, introns, and other elements described herein that direct the expression of a nucleic acid sequence or coding sequence that is operably linked thereto. The term "promoter" will be used herein to refer to a group of transcriptional control modules that are clustered around the initiation site for RNA polymerase II and that when operationally linked to the protein coding sequences of the invention lead to the expression of the encoded protein. The expression of the transgenes of the present invention can be under the control of a constitutive promoter or of an inducible promoter, which initiates transcription only when exposed to some particular external stimulus, such as, without limitation, antibiotics such as tetracycline, hormones such as ecdysone, or heavy metals. The promoter can also be specific to a particular cell-type, tissue or organ. Many suitable promoters and enhancers are known in the art, and any such suitable promoter or enhancer may be used for expression of the transgenes of the invention. For example, suitable promoters and/or enhancers can be selected from the Eukaryotic Promoter Database (EPDB).

The present invention relates to a recombinant viral vector expressing a foreign epitope. Advantageously, the epitope is an HIV epitope. In an advantageous embodiment, the HIV epitope is a protein fragment of the present invention, however, the present invention may encompass additional HIV antigens, epitopes or immunogens. Advantageously, the HIV epitope is an HIV antigen including but not limited to, the HIV antigens of U.S. Pat. Nos. 7,341,731; 7,335,364; 7,329,807; 7,323,553; 7,320,859; 7,311,920; 7,306,798; 7,285,646; 7,285,289; 7,285,271; 7,282,364; 7,273,695; 7,270,997; 7,262,270; 7,244,819; 7,244,575; 7,232,567; 7,232,566; 7,223,844; 7,223,739; 7,223,534; 7,223,368; 7,220,554; 7,214,530; 7,211,659; 7,211,432; 7,205,159; 7,198,934; 7,195,768; 7,192,555; 7,189,826; 7,189,522; 7,186,507; 7,179,645; 7,175,843; 7,172,761; 7,169,550; 7,157,083; 7,153,509; 7,147,862; 7,141,550; 7,129,219; 7,122,188; 7,118,859; 7,118,855; 7,118,751; 7,118,742; 7,105,655; 7,101,552; 7,097,971; 7,097,842; 7,094,405; 7,091,049; 7,090,648; 7,087,377; 7,083,787; 7,070,787; 7,070,781; 7,060,273; 7,056,521; 7,056,519; 7,049,136; 7,048,929; 7,033,593; 7,030,094; 7,022,326; 7,009,037; 7,008,622; 7,001,759; 6,997,863; 6,995,008; 6,979,535; 6,974,574; 6,972,126; 6,969,609; 6,964,769; 6,964,762; 6,958,158; 6,956,059; 6,953,689; 6,951,648; 6,946,075; 6,927,031; 6,919,319; 6,919,318; 6,919,077; 6,913,752; 6,911,315; 6,908,617; 6,908,612; 6,902,743; 6,900,010; 6,893,869; 6,884,785; 6,884,435; 6,875,435; 6,867,005; 6,861,234; 6,855,539; 6,841,381; 6,841,345; 6,838,477; 6,821,955; 6,818,392; 6,818,222; 6,815,217; 6,815,201; 6,812,026; 6,812,025; 6,812,024; 6,808,923; 6,806,055; 6,803,231; 6,800,613; 6,800,288; 6,797,811; 6,780,967; 6,780,598; 6,773,920; 6,764,682; 6,761,893; 6,753,015; 6,750,005; 6,737,239; 6,737,067; 6,730,304; 6,720,310; 6,716,823; 6,713,301; 6,713,070; 6,706,859; 6,699,722; 6,699,656; 6,696,291; 6,692,745; 6,670,181; 6,670,115; 6,664,406; 6,657,055; 6,657,050; 6,656,471; 6,653,066; 6,649,409; 6,649,372; 6,645,732; 6,641,816; 6,635,469; 6,613,530; 6,605,427; 6,602,709; 6,602,705; 6,600,023; 6,596,477; 6,596,172; 6,593,103; 6,593,079; 6,579,673; 6,576,758; 6,573,245; 6,573,040; 6,569,418; 6,569,340; 6,562,800; 6,558,961; 6,551,828; 6,551,824; 6,548,275; 6,544,780; 6,544,752; 6,544,728; 6,534,482; 6,534,312; 6,534,064; 6,531,572; 6,531,313; 6,525,179; 6,525,028; 6,524,582; 6,521,449; 6,518,030; 6,518,015; 6,514,691; 6,514,503; 6,511,845; 6,511,812; 6,511,801; 6,509,313; 6,506,384; 6,503,882; 6,495,676; 6,495,526; 6,495,347; 6,492,123; 6,489,131; 6,489,129; 6,482,614; 6,479,286; 6,479,284; 6,465,634; 6,461,615; 6,458,560; 6,458,527; 6,458,370; 6,451,601; 6,451,592; 6,451,323; 6,436,407; 6,432,633; 6,428,970; 6,428,952; 6,428,790; 6,420,139; 6,416,997; 6,410,318; 6,410,028; 6,410,014; 6,407,221; 6,406,710; 6,403,092; 6,399,295; 6,392,013; 6,391,657; 6,384,198; 6,380,170; 6,376,170; 6,372,426; 6,365,187; 6,358,739; 6,355,248; 6,355,247; 6,348,450; 6,342,372; 6,342,228; 6,338,952; 6,337,179; 6,335,183; 6,335,017; 6,331,404; 6,329,202; 6,329,173; 6,328,976; 6,322,964; 6,319,666; 6,319,665; 6,319,500; 6,319,494; 6,316,205; 6,316,003; 6,309,633; 6,306,625; 6,296,807; 6,294,322; 6,291,239; 6,291,157; 6,287,568; 6,284,456; 6,284,194; 6,274,337; 6,270,956; 6,270,769; 6,268,484; 6,265,562; 6,265,149; 6,262,029; 6,261,762; 6,261,571; 6,261,569; 6,258,599; 6,258,358; 6,248,332; 6,245,331; 6,242,461; 6,241,986; 6,235,526; 6,235,466; 6,232,120; 6,228,361; 6,221,579; 6,214,862; 6,214,804; 6,210,963; 6,210,873; 6,207,185; 6,203,974; 6,197,755; 6,197,531; 6,197,496; 6,194,142; 6,190,871; 6,190,666; 6,168,923; 6,156,302; 6,153,408; 6,153,393; 6,153,392; 6,153,378; 6,153,377; 6,146,635; 6,146,614; 6,143,876; 6,140,059; 6,140,043; 6,139,746; 6,132,992; 6,124,306; 6,124,132; 6,121,006; 6,120,990; 6,114,507; 6,114,143; 6,110,466; 6,107,020; 6,103,521; 6,100,234; 6,099,848; 6,099,847; 6,096,291; 6,093,405; 6,090,392; 6,087,476; 6,083,903; 6,080,846; 6,080,725; 6,074,650; 6,074,646; 6,070,126; 6,063,905; 6,063,564; 6,060,256; 6,060,064; 6,048,530; 6,045,788; 6,043,347; 6,043,248; 6,042,831; 6,037,165; 6,033,672; 6,030,772; 6,030,770; 6,030,618; 6,025,141; 6,025,125; 6,020,468; 6,019,979; 6,017,543; 6,017,537; 6,015,694; 6,015,661; 6,013,484; 6,013,432; 6,007,838; 6,004,811; 6,004,807; 6,004,763; 5,998,132; 5,993,819; 5,989,806; 5,985,926; 5,985,641; 5,985,545; 5,981,537; 5,981,505; 5,981,170; 5,976,551; 5,972,339; 5,965,371; 5,962,428; 5,962,318; 5,961,979; 5,961,970; 5,958,765; 5,958,422; 5,955,647; 5,955,342; 5,951,986; 5,951,975; 5,942,237; 5,939,277; 5,939,074; 5,935,580; 5,928,930; 5,928,913; 5,928,644; 5,928,642; 5,925,513; 5,922,550; 5,922,325; 5,919,458; 5,916,806; 5,916,563; 5,914,395; 5,914,109; 5,912,338; 5,912,176; 5,912,170; 5,906,936; 5,895,650; 5,891,623; 5,888,726; 5,885,580; 5,885,578; 5,879,685; 5,876,731; 5,876,716; 5,874,226; 5,872,012; 5,871,747; 5,869,058; 5,866,694; 5,866,341; 5,866,320; 5,866,319; 5,866,137; 5,861,290; 5,858,740; 5,858,647; 5,858,646; 5,858,369; 5,858,368; 5,858,366; 5,856,185; 5,854,400; 5,853,736; 5,853,725; 5,853,724; 5,852,186; 5,851,829; 5,851,529; 5,849,475; 5,849,288; 5,843,728; 5,843,723; 5,843,640; 5,843,635; 5,840,480; 5,837,510; 5,837,250; 5,837,242; 5,834,599; 5,834,441; 5,834,429; 5,834,256; 5,830,876; 5,830,641; 5,830,475; 5,830,458; 5,830,457; 5,827,749; 5,827,723; 5,824,497; 5,824,304; 5,821,047; 5,817,767; 5,817,754; 5,817,637; 5,817,470; 5,817,318; 5,814,482; 5,807,707; 5,804,604; 5,804,371; 5,800,822; 5,795,955; 5,795,743; 5,795,572; 5,789,388; 5,780,279; 5,780,038; 5,776,703; 5,773,260; 5,770,572; 5,766,844; 5,766,842; 5,766,625; 5,763,574; 5,763,190; 5,762,965; 5,759,769; 5,756,666; 5,753,258; 5,750,373; 5,747,641; 5,747,526; 5,747,028; 5,736,320; 5,736,146; 5,733,760; 5,731,189; 5,728,385; 5,721,095; 5,716,826; 5,716,637; 5,716,613; 5,714,374; 5,709,879; 5,709,860; 5,709,843; 5,705,331; 5,703,057; 5,702,707; 5,698,178; 5,688,914; 5,686,078; 5,681,831; 5,679,784; 5,674,984; 5,672,472; 5,667,964; 5,667,783; 5,665,536; 5,665,355; 5,660,990; 5,658,745; 5,658,569; 5,643,756; 5,641,624; 5,639,854; 5,639,598; 5,637,677; 5,637,455; 5,633,234; 5,629,153; 5,627,025; 5,622,705; 5,614,413; 5,610,035; 5,607,831; 5,606,026; 5,601,819; 5,597,688; 5,593,972; 5,591,829; 5,591,823; 5,589,466; 5,587,285; 5,585,254; 5,585,250; 5,580,773; 5,580,739; 5,580,563; 5,573,916; 5,571,667; 5,569,468; 5,558,865; 5,556,745; 5,550,052; 5,543,328; 5,541,100; 5,541,057; 5,534,406; 5,529,765; 5,523,232; 5,516,895; 5,514,541; 5,510,264; 5,500,161; 5,480,967; 5,480,966; 5,470,701; 5,468,606; 5,462,852; 5,459,127; 5,449,601; 5,447,838; 5,447,837; 5,439,809; 5,439,792;

5,418,136; 5,399,501; 5,397,695; 5,391,479; 5,384,240; 5,374,519; 5,374,518; 5,374,516; 5,364,933; 5,359,046; 5,356,772; 5,354,654; 5,344,755; 5,335,673; 5,332,567; 5,320,940; 5,317,009; 5,312,902; 5,304,466; 5,296,347; 5,286,852; 5,268,265; 5,264,356; 5,264,342; 5,260,308; 5,256,767; 5,256,561; 5,252,556; 5,230,998; 5,230,887; 5,227,159; 5,225,347; 5,221,610; 5,217,861; 5,208,321; 5,206,136; 5,198,346; 5,185,147; 5,178,865; 5,173,400; 5,173,399; 5,166,050; 5,156,951; 5,135,864; 5,122,446; 5,120,662; 5,103,836; 5,100,777; 5,100,662; 5,093,230; 5,077,284; 5,070,010; 5,068,174; 5,066,782; 5,055,391; 5,043,262; 5,039,604; 5,039,522; 5,030,718; 5,030,555; 5,030,449; 5,019,387; 5,013,556; 5,008,183; 5,004,697; 4,997,772; 4,983,529; 4,983,387; 4,965,069; 4,945,082; 4,921,787; 4,918,166; 4,900,548; 4,888,290; 4,886,742; 4,885,235; 4,870,003; 4,869,903; 4,861,707; 4,853,326; 4,839,288; 4,833,072 and 4,795,739.

In another embodiment, HIV, or immunogenic fragments thereof, may be utilized as the HIV epitope. For example, the HIV nucleotides of U.S. Pat. Nos. 7,393,949, 7,374,877, 7,306,901, 7,303,754, 7,173,014, 7,122,180, 7,078,516, 7,022,814, 6,974,866, 6,958,211, 6,949,337, 6,946,254, 6,896,900, 6,887,977, 6,870,045, 6,803,187, 6,794,129, 6,773,915, 6,768,004, 6,706,268, 6,696,291, 6,692,955, 6,656,706, 6,649,409, 6,627,442, 6,610,476, 6,602,705, 6,582,920, 6,557,296, 6,531,587, 6,531,137, 6,500,623, 6,448,078, 6,429,306, 6,420,545, 6,410,013, 6,407,077, 6,395,891, 6,355,789, 6,335,158, 6,323,185, 6,316,183, 6,303,293, 6,300,056, 6,277,561, 6,270,975, 6,261,564, 6,225,045, 6,222,024, 6,194,391, 6,194,142, 6,162,631, 6,114,167, 6,114,109, 6,090,392, 6,060,587, 6,057,102, 6,054,565, 6,043,081, 6,037,165, 6,034,233, 6,033,902, 6,030,769, 6,020,123, 6,015,661, 6,010,895, 6,001,555, 5,985,661, 5,980,900, 5,972,596, 5,939,538, 5,912,338, 5,869,339, 5,866,701, 5,866,694, 5,866,320, 5,866,137, 5,864,027, 5,861,242, 5,858,785, 5,858,651, 5,849,475, 5,843,638, 5,840,480, 5,821,046, 5,801,056, 5,786,177, 5,786,145, 5,773,247, 5,770,703, 5,756,674, 5,741,706, 5,705,612, 5,693,752, 5,688,637, 5,688,511, 5,684,147, 5,665,577, 5,585,263, 5,578,715, 5,571,712, 5,567,603, 5,554,528, 5,545,726, 5,527,895, 5,527,894, 5,223,423, 5,204,259, 5,144,019, 5,051,496 and 4,942,122 are useful for the present invention.

Any epitope recognized by an HIV antibody may be used in the present invention. For example, the anti-HIV antibodies of U.S. Pat. Nos. 6,949,337, 6,900,010, 6,821,744, 6,768,004, 6,613,743, 6,534,312, 6,511,830, 6,489,131, 6,242,197, 6,114,143, 6,074,646, 6,063,564, 6,060,254, 5,919,457, 5,916,806, 5,871,732, 5,824,304, 5,773,247, 5,736,320, 5,637,455, 5,587,285, 5,514,541, 5,317,009, 4,983,529, 4,886,742, 4,870,003 and 4,795,739 are useful for the present invention. Furthermore, monoclonal anti-HIV antibodies of U.S. Pat. Nos. 7,074,556, 7,074,554, 7,070,787, 7,060,273, 7,045,130, 7,033,593, RE39,057, 7,008,622, 6,984,721, 6,972,126, 6,949,337, 6,946,465, 6,919,077, 6,916,475, 6,911,315, 6,905,680, 6,900,010, 6,825,217, 6,824,975, 6,818,392, 6,815,201, 6,812,026, 6,812,024, 6,797,811, 6,768,004, 6,703,019, 6,689,118, 6,657,050, 6,608,179, 6,600,023, 6,596,497, 6,589,748, 6,569,143, 6,548,275, 6,525,179, 6,524,582, 6,506,384, 6,498,006, 6,489,131, 6,465,173, 6,461,612, 6,458,933, 6,432,633, 6,410,318, 6,406,701, 6,395,275, 6,391,657, 6,391,635, 6,384,198, 6,376,170, 6,372,217, 6,344,545, 6,337,181, 6,329,202, 6,319,665, 6,319,500, 6,316,003, 6,312,931, 6,309,880, 6,296,807, 6,291,239, 6,261,558, 6,248,514, 6,245,331, 6,242,197, 6,241,986, 6,228,361, 6,221,580, 6,190,871, 6,177,253, 6,146,635, 6,146,627, 6,146,614, 6,143,876, 6,132,992, 6,124,132, RE36,866, 6,114,143, 6,103,238, 6,060,254, 6,039,684, 6,030,772, 6,020,468, 6,013,484, 6,008,044, 5,998,132, 5,994,515, 5,993,812, 5,985,545, 5,981,278, 5,958,765, 5,939,277, 5,928,930, 5,922,325, 5,919,457, 5,916,806, 5,914,109, 5,911,989, 5,906,936, 5,889,158, 5,876,716, 5,874,226, 5,872,012, 5,871,732, 5,866,694, 5,854,400, 5,849,583, 5,849,288, 5,840,480, 5,840,305, 5,834,599, 5,831,034, 5,827,723, 5,821,047, 5,817,767, 5,817,458, 5,804,440, 5,795,572, 5,783,670, 5,776,703, 5,773,225, 5,766,944, 5,753,503, 5,750,373, 5,747,641, 5,736,341, 5,731,189, 5,707,814, 5,702,707, 5,698,178, 5,695,927, 5,665,536, 5,658,745, 5,652,138, 5,645,836, 5,635,345, 5,618,922, 5,610,035, 5,607,847, 5,604,092, 5,601,819, 5,597,896, 5,597,688, 5,591,829, 5,558,865, 5,514,541, 5,510,264, 5,478,753, 5,374,518, 5,374,516, 5,344,755, 5,332,567, 5,300,433, 5,296,347, 5,286,852, 5,264,221, 5,260,308, 5,256,561, 5,254,457, 5,230,998, 5,227,159, 5,223,408, 5,217,895, 5,180,660, 5,173,399, 5,169,752, 5,166,050, 5,156,951, 5,140,105, 5,135,864, 5,120,640, 5,108,904, 5,104,790, 5,049,389, 5,030,718, 5,030,555, 5,004,697, 4,983,529, 4,888,290, 4,886,742 and 4,853,326, are also useful for the present invention.

In one example, the epitope is an SIV epitope. It is understood by one of skill in the art that anything referring to HIV in the specification also applies to SIV. In an advantageous embodiment, the SIV epitope is a protein fragment of the present invention, however, the present invention may encompass additional SIV antigens, epitopes or immunogens. Advantageously, the SIV epitope is an SIV antigen, including but not limited to, the SIV antigens of U.S. Pat. Nos. 7,892,729; 7,886,962; 7,879,914; 7,829,287; 7,794,998; 7,767,455; 7,759,477; 7,758,869; 7,754,420; 7,749,973; 7,748,618; 7,732,124; 7,709,606; 7,700,342; 7,700,273; 7,625,917; 7,622,124; 7,611,721; 7,608,422; 7,601,518; 7,585,675; 7,534,603; 7,511,117; 7,508,781; 7,507,417; 7,479,497; 7,464,352; 7,457,973; 7,442,551; 7,439,052; 7,419,829; 7,407,663; 7,378,515; 7,364,760; 7,312,065; 7,261,876; 7,220,554; 7,211,240; 7,198,935; 7,169,394; 7,098,201; 7,078,516; 7,070,993; 7,048,929; 7,034,010; RE39,057; 7,022,814; 7,018,638; 6,955,919; 6,933,377; 6,908,617; 6,902,929; 6,846,477; 6,818,442; 6,803,231; 6,800,281; 6,797,811; 6,790,657; 6,712,612; 6,706,729; 6,703,394; 6,682,907; 6,656,706; 6,645,956; 6,635,472; 6,596,539; 6,589,763; 6,562,571; 6,555,523; 6,555,342; 6,541,009; 6,531,574; 6,531,123; 6,503,713; 6,479,281; 6,475,718; 6,469,083; 6,468,539; 6,455,265; 6,448,390; 6,440,730; 6,423,544; 6,365,150; 6,362,000; 6,326,007; 6,322,969; 6,291,664; 6,277,601; 6,261,571; 6,255,312; 6,207,455; 6,194,142; 6,117,656; 6,111,087; 6,107,020; 6,080,846; 6,060,064; 6,046,228; 6,043,081; 6,027,731; 6,020,123; 6,017,536; 6,004,781; 5,994,515; 5,981,259; 5,961,976; 5,950,176; 5,929,222; 5,928,913; 5,912,176; 5,888,726; 5,861,243; 5,861,161; 5,858,366; 5,830,475; 5,817,316; 5,804,196; 5,786,177; 5,759,768; 5,747,324; 5,705,522; 5,705,331; 5,698,446; 5,688,914; 5,688,637; 5,654,195; 5,650,269; 5,631,154; 5,582,967; 5,552,269; 5,512,281; 5,508,166; 5,470,572; 5,312,902; 5,310,651; 5,268,265; 5,254,457; 5,212,084; 5,087,631 and 4,978,687.

The vectors used in accordance with the present invention should typically be chosen such that they contain a suitable gene regulatory region, such as a promoter or enhancer, such that the antigens of the invention can be expressed.

When the aim is to express antigens of the invention in vivo in a subject, for example in order to generate an immune response against an HIV-1 antigen and/or protective immunity against HIV-1, expression vectors that are suitable for expression on that subject, and that are safe for use in vivo, should be chosen. For example, in some embodiments it may be desired to express the antibodies and/or antigens of the invention in a laboratory animal, such as for pre-clinical testing of the HIV-1 immunogenic compositions and vaccines of the invention. In other embodiments, it will be desirable to express the antigens of the invention in human subjects, such as in clinical trials and for actual clinical use of the immunogenic compositions and vaccine of the invention. Any vectors that are suitable for such uses can be employed, and it is well within the capabilities of the skilled artisan to select a suitable vector. In some embodiments it may be preferred that the vectors used for these in vivo applications are attenuated to vector from amplifying in the subject. For example, if plasmid vectors are used, preferably they will lack an origin of replication that functions in the subject so as to enhance safety for in vivo use in the subject. If viral vectors are used, preferably they are attenuated or replication-defective in the subject, again, so as to enhance safety for in vivo use in the subject.

In preferred embodiments of the present invention viral vectors are used. Advantageously, the vector is a CMV vector, preferably lacking at least the glycoprotein US11.

In preferred embodiments, the viral vectors of the invention are administered in vivo, for example where the aim is to produce an immunogenic response in a subject. For example, in some embodiments it may be desired to express the transgenes of the invention in a laboratory animal, such as for pre-clinical testing of the HIV-1 immunogenic compositions and vaccines of the invention. In other embodiments, it will be desirable to express the antibodies and/or antigens of the invention in human subjects, such as in clinical trials and for actual clinical use of the immunogenic compositions and vaccine of the invention. In preferred embodiments the subject is a human, for example a human that is infected with, or is at risk of infection with, HIV-1.

For such in vivo applications the nucleotide sequences, antibodies and/or antigens of the invention are preferably administered as a component of an immunogenic composition which may comprise the nucleotide sequences and/or antigens of the invention in admixture with a pharmaceutically acceptable carrier. The immunogenic compositions of the invention are useful to stimulate an immune response against HIV-1 and may be used as one or more components of a prophylactic or therapeutic vaccine against HIV-1 for the prevention, amelioration or treatment of AIDS. The nucleic acids and vectors of the invention are particularly useful for providing genetic vaccines, i.e. vaccines for delivering the nucleic acids encoding the antigens of the invention to a subject, such as a human, such that the antigens are then expressed in the subject to elicit an immune response.

The compositions of the invention may be injectable suspensions, solutions, sprays, lyophilized powders, syrups, elixirs and the like. Any suitable form of composition may be used. To prepare such a composition, a nucleic acid or vector of the invention, having the desired degree of purity, is mixed with one or more pharmaceutically acceptable carriers and/or excipients. The carriers and excipients must be "acceptable" in the sense of being compatible with the other ingredients of the composition. Acceptable carriers, excipients, or stabilizers are nontoxic to recipients at the dosages and concentrations employed, and include, but are not limited to, water, saline, phosphate buffered saline, dextrose, glycerol, ethanol, or combinations thereof, buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN® PLURONICS® or polyethylene glycol (PEG).

An immunogenic or immunological composition can also be formulated in the form of an oil-in-water emulsion. The oil-in-water emulsion can be based, for example, on light liquid paraffin oil (European Pharmacopea type); isoprenoid oil such as squalane, squalene, EICOSANE™ or tetratetracontane; oil resulting from the oligomerization of alkene(s), e.g., isobutene or decene; esters of acids or of alcohols containing a linear alkyl group, such as plant oils, ethyl oleate, propylene glycol di(caprylate/caprate), glyceryl tri (caprylate/caprate) or propylene glycol dioleate; esters of branched fatty acids or alcohols, e.g., isostearic acid esters. The oil advantageously is used in combination with emulsifiers to form the emulsion. The emulsifiers can be nonionic surfactants, such as esters of sorbitan, mannide (e.g., anhydromannitol oleate), glycerol, polyglycerol, propylene glycol, and oleic, isostearic, ricinoleic, or hydroxystearic acid, which are optionally ethoxylated, and polyoxypropylene-polyoxyethylene copolymer blocks, such as the Pluronic® products, e.g., L121. The adjuvant can be a mixture of emulsifier(s), micelle-forming agent, and oil such as that which is commercially available under the name Provax® (IDEC Pharmaceuticals, San Diego, Calif.).

The immunogenic compositions of the invention can contain additional substances, such as wetting or emulsifying agents, buffering agents, or adjuvants to enhance the effectiveness of the vaccines (Remington's Pharmaceutical Sciences, 18th edition, Mack Publishing Company, (ed.) 1980).

Adjuvants may also be included. Adjuvants include, but are not limited to, mineral salts (e.g., AlK(SO$_4$)$_2$, AlNa (SO$_4$)$_2$, AlNH(SO$_4$)$_2$, silica, alum, Al(OH)$_3$, Ca$_3$(PO$_4$)$_2$, kaolin, or carbon), polynucleotides with or without immune stimulating complexes (ISCOMs) (e.g., CpG oligonucleotides, such as those described in Chuang, T. H. et al., (2002) J. Leuk. Biol. 71(3): 538-44; Ahmad-Nejad, P. et al. (2002) Eur. J. Immunol. 32(7): 1958-68; poly IC or poly AU acids, polyarginine with or without CpG (also known in the art as IC31; see Schellack, C. et al. (2003) Proceedings of the 34th Annual Meeting of the German Society of Immunology; Lingnau, K. et al. (2002) Vaccine 20(29-30): 3498-508), JuvaVax (U.S. Pat. No. 6,693,086), certain natural substances (e.g., wax D from *Mycobacterium tuberculosis*, substances found in Cornyebacterium parvum, *Bordetella pertussis*, or members of the genus Brucella), flagellin (Toll-like receptor 5 ligand; see McSorley, S. J. et al. (2002) J. Immunol. 169(7): 3914-9), saponins such as Q521, Q517, and QS7 (U.S. Pat. Nos. 5,057,540; 5,650,398; 6,524,584; 6,645,495), monophosphoryl lipid A, in particular, 3-de-O-acylated monophosphoryl lipid A (3D-MPL), imiquimod (also known in the art as IQM and commercially available as Aldara®); U.S. Pat. Nos. 4,689,338; 5,238,944; Zuber, A. K. et al. (2004) 22(13-14): 1791-8), and the CCR5 inhibitor CMPD167 (see Veazey, R. S. et al. (2003) J. Exp. Med. 198: 1551-1562). Aluminum hydroxide or phosphate(alum) are commonly used at 0.05 to 0.1% solution in phosphate buffered saline. Other adjuvants that can be used, especially with DNA vaccines, are cholera toxin, especially CTA1-DD/ISCOMs (see Mowat, A. M. et al. (2001) J. Immunol. 167(6): 3398-405), polyphosphazenes (Allcock, H. R. (1998) App. Organometallic Chem. 12(10-11): 659-666; Payne, L. G. et al. (1995) Pharm. Biotechnol. 6: 473-93), cytokines such as, but not limited to, IL-2, IL-4, GM-CSF, IL-12, IL-15 IGF-1, IFN-α, IFN-β, and IFN-γ (Boyer et al., (2002) J. Liposome Res. 121:137-142; WO01/095919), immunoregulatory proteins such as CD40L (ADX40; see, for example, WO03/063899), and the CD1a ligand of natural killer cells (also known as CRONY or α-galactosyl ceramide; see Green, T. D. et al., (2003) J. Virol. 77(3): 2046-2055), immunostimulatory fusion proteins such as IL-2 fused to the Fc fragment of immunoglobulins (Barouch et al., Science 290:486-492, 2000) and co-stimulatory molecules B7.1 and B7.2 (Boyer), all of which can be administered either as proteins or in the form of DNA, in the same viral vectors as those encoding the antigens of the invention or on separate expression vectors. Alternatively, vaccines of the invention may be provided and administered without any adjuvants.

The immunogenic compositions can be designed to introduce the viral vectors to a desired site of action and release it at an appropriate and controllable rate. Methods of preparing controlled-release formulations are known in the art. For example, controlled release preparations can be produced by the use of polymers to complex or absorb the immunogen and/or immunogenic composition. A controlled-release formulation can be prepared using appropriate macromolecules (for example, polyesters, polyamino acids, polyvinyl, pyrrolidone, ethylenevinylacetate, methylcellulose, carboxymethylcellulose, or protamine sulfate) known to provide the desired controlled release characteristics or release profile. Another possible method to control the duration of action by a controlled-release preparation is to incorporate the active ingredients into particles of a polymeric material such as, for example, polyesters, polyamino acids, hydrogels, polylactic acid, polyglycolic acid, copolymers of these acids, or ethylene vinylacetate copolymers. Alternatively, instead of incorporating these active ingredients into polymeric particles, it is possible to entrap these materials into microcapsules prepared, for example, by coacervation techniques or by interfacial polymerization, for example, hydroxymethylcellulose or gelatin-microcapsule and poly-(methylmethacrylate) microcapsule, respectively, in colloidal drug delivery systems (for example, liposomes, albumin microspheres, microemulsions, nano-particles and nanocapsules) or in macroemulsions. Such techniques are disclosed in New Trends and Developments in Vaccines, Voller et al. (eds.), University Park Press, Baltimore, Md., 1978 and Remington's Pharmaceutical Sciences, 16th edition.

Suitable dosages of the viral vectors of the invention (collectively, the immunogens) in the immunogenic composition of the invention can be readily determined by those of skill in the art. For example, the dosage of the immunogens can vary depending on the route of administration and the size of the subject. Suitable doses can be determined by those of skill in the art, for example by measuring the immune response of a subject, such as a laboratory animal, using conventional immunological techniques, and adjusting the dosages as appropriate. Such techniques for measuring the immune response of the subject include but are not limited to, chromium release assays, tetramer binding assays, IFN-γ ELISPOT assays, IL-2 ELISPOT assays, intracellular cytokine assays, and other immunological detection assays, e.g., as detailed in the text "Antibodies: A Laboratory Manual" by Ed Harlow and David Lane.

The immunogenic compositions can be administered using any suitable delivery method including, but not limited to, intramuscular, intravenous, intradermal, mucosal, and topical delivery. Such techniques are well known to those of skill in the art. More specific examples of delivery methods are intramuscular injection, intradermal injection, and subcutaneous injection. However, delivery need not be limited to injection methods.

Immunization schedules (or regimens) are well known for animals (including humans) and can be readily determined for the particular subject and immunogenic composition. Hence, the immunogens can be administered one or more times to the subject. Preferably, there is a set time interval between separate administrations of the immunogenic composition. While this interval varies for every subject, typically it ranges from 10 days to several weeks, and is often 2, 4, 6 or 8 weeks. For humans, the interval is typically from 2 to 6 weeks. In a particularly advantageous embodiment of the present invention, the interval is longer, advantageously about 10 weeks, 12 weeks, 14 weeks, 16 weeks, 18 weeks, 20 weeks, 22 weeks, 24 weeks, 26 weeks, 28 weeks, 30 weeks, 32 weeks, 34 weeks, 36 weeks, 38 weeks, 40 weeks, 42 weeks, 44 weeks, 46 weeks, 48 weeks, 50 weeks, 52 weeks, 54 weeks, 56 weeks, 58 weeks, 60 weeks, 62 weeks, 64 weeks, 66 weeks, 68 weeks or 70 weeks.

The immunization regimes typically have from 1 to 6 administrations of the immunogenic composition, but may have as few as one or two or four. The methods of inducing an immune response can also include administration of an adjuvant with the immunogens. In some instances, annual, biannual or other long interval (5-10 years) booster immunization can supplement the initial immunization protocol.

The present methods also include a variety of prime-boost regimens, for example DNA prime-Adenovirus boost regimens. In these methods, one or more priming immunizations are followed by one or more boosting immunizations. The actual immunogenic composition can be the same or different for each immunization and the type of immunogenic composition (e.g., containing protein or expression vector), the route, and formulation of the immunogens can also be varied. For example, if an expression vector is used for the priming and boosting steps, it can either be of the same or different type (e.g., DNA or bacterial or viral expression vector). One useful prime-boost regimen provides for two priming immunizations, four weeks apart, followed by two boosting immunizations at 4 and 8 weeks after the last priming immunization. It should also be readily apparent to one of skill in the art that there are several permutations and combinations that are encompassed using the DNA, bacterial and viral expression vectors of the invention to provide priming and boosting regimens. In the event that the viral vectors express US2-11 or some of the genes encoded in the US2-11 region they can be used repeatedly while expressing different antigens derived from different pathogens.

A specific embodiment of the invention provides methods of inducing an immune response against a pathogen in a subject by administering an immunogenic composition of the invention, preferably a CMV vector with a deleterious mutation in at least US11 encoding one or more of the epitopes of the invention, one or more times to a subject wherein the epitopes are expressed at a level sufficient to induce a specific immune response in the subject. Such immunizations can be repeated multiple times at time intervals of at least 2, 4 or 6 weeks (or more) in accordance with a desired immunization regime.

The immunogenic compositions of the invention can be administered alone, or can be co-administered, or sequentially administered, with other antigens, e.g., with "other" immunological, antigenic or vaccine or therapeutic compositions thereby providing multivalent or "cocktail" or combination compositions of the invention and methods of employing them. Again, the ingredients and manner (sequential or co-administration) of administration, as well as dosages can be determined taking into consideration such factors as the age, sex, weight, species and condition of the particular subject, and the route of administration.

When used in combination, the other antigens can be administered at the same time or at different times as part of an overall immunization regime, e.g., as part of a prime-boost regimen or other immunization protocol. In an advantageous embodiment, the other HIV immunogen is env, preferably the HIV env trimer.

Although the present invention and its advantages have been described in detail, it should be understood that various changes, substitutions and alterations can be made herein without departing from the spirit and scope of the invention as defined in the appended claims.

EXAMPLES

Example 1: Recombinant Cytomegalovirus Vectors with Improved Immunogenicity

Figure 1:
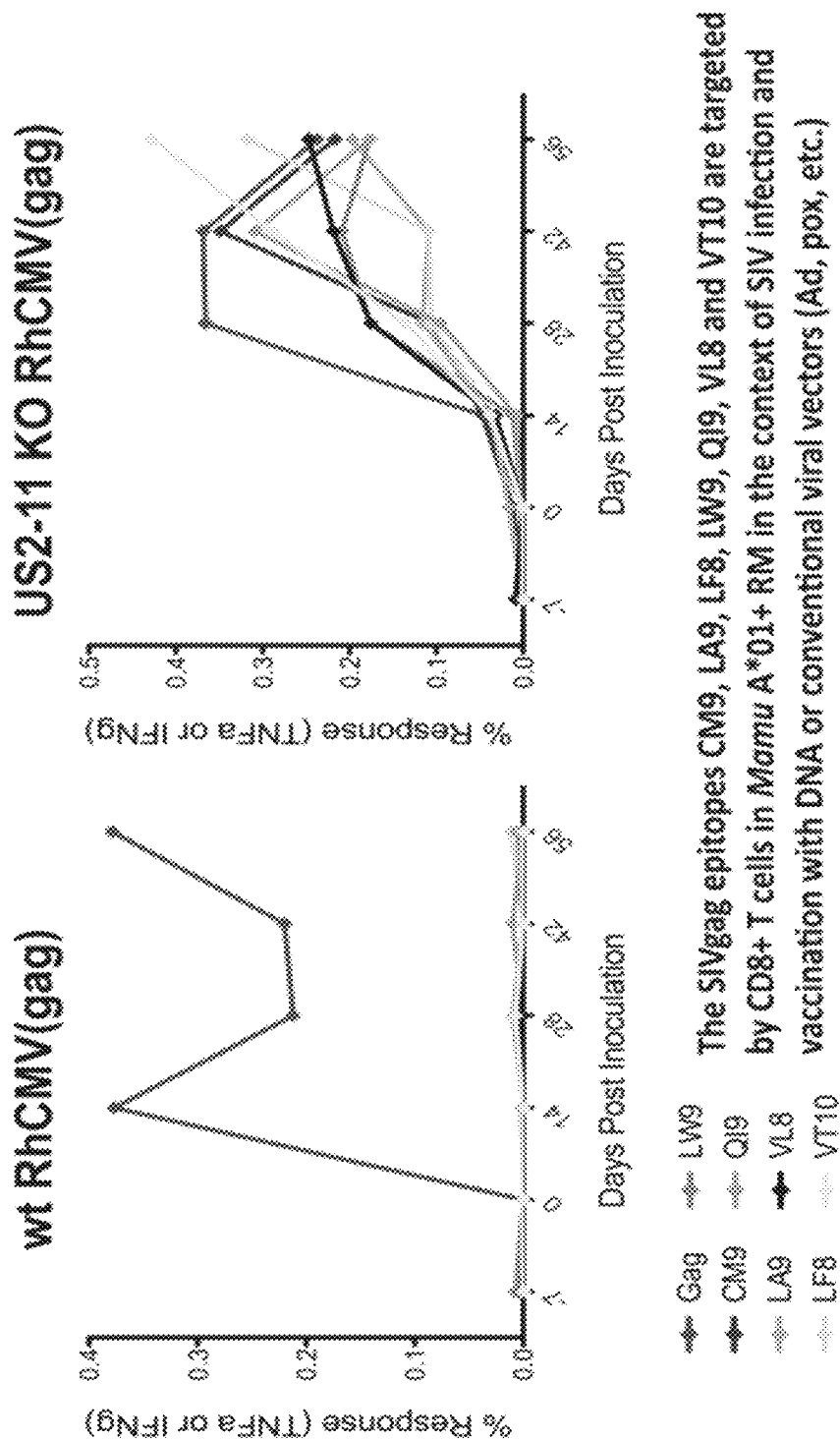
FIG. 1 depicts a set of two line graphs that compares CD8+ T cell epitope targeting of SIVgag-specific responses arising after vaccination of Mamu A*01+, CMV-naïve RM with wt vs. US2-11 knock-out (KO) RhCMV/gag vectors. The US2-11 KO vector elicits responses to all previously characterized Mamu A*01-restricted gag epitopes, whereas wt CMV vectors elicit gag-specific CD8+ T cell responses that do not target these epitopes (gag=total gag 15 mer mixes).

During the course of evaluation of Rhesus macaque (Rh) CMV/SIV vector immunogenicity, SIV epitopes that had been previously shown to represent dominant targets of CD8+ T cells in SIV-infected or DNA/Adenovirus/pox vector-vaccinated Rhesus macaques were not targeted at all by RhCMV/SIV vector-elicited CD8+ T cell responses (by ICS or tetramer staining) These included 9 Mamu A*01-restricted epitopes in 12 animals; 3 Mamu A*02 epitopes in 4 animals, 1 B*08-epitope in 1 animal, and 3 Mamu B*17-epitopes in 7 animals (FIG. 1; left). HCMV and RhCMV express 4 related glycoproteins—US2/Rh182, US3/Rh184, US6/Rh185 and US11/Rh189—that act together with very high efficiency to inhibit presentation of MHC class I-restricted epitopes by infected cells Powers C et al., Curr Top Microbiol Immunol 325, 333-359 (2008); Liu Z et al., Int J Biochem Cell Biol 41, 503-506 (2009); van der Wal, F J et al., Curr Top Microbiol Immunol 269, 37-55 (2002); Hewitt E W et al., EMBO J 20, 387-396 (2001); all of which are incorporated by reference herein.

Figure 3:
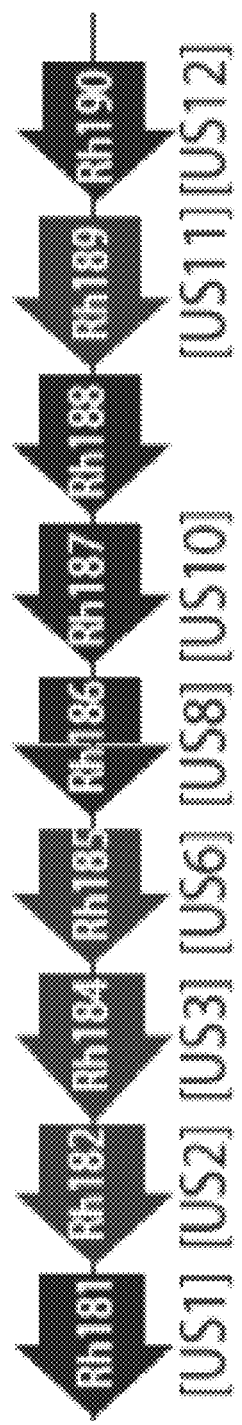
FIG. 3 depicts the RhCMV US2-11 region. MHC-I inhibitors are Rh182, Rh184, Rh185 and Rh189. Human CMV homologues are shown below.

The US2-11 region of CMV is shown in FIG. 3. Applicants have generated one vector that may comprise a deletion encompassing the US2, US3, and US6 (ΔUS2-6) genes and another that may comprise a deletion of US8, US10, and US11 (ΔUS8-11). Each vector may be generated by BAC-mutagenesis, as described in Hansen S G et al., 2010 supra. Other constructs may comprise SIVgag, SIVenv, SIVretanef (rtn), SIVpol, or other exogenous viral, bacterial, parasitic or cancer-derived antigens in place of US2-US6 or US8-11. Additional constructs include individual mutations and/or deletions of US2, US3, US6, US8, US10 or US11 with the rest of US2-11 intact. Such constructs may also include exogenous antigens.

Example 2—Construction and Characterization of RhCMVΔUS2-6 and RhCMVΔUS8-11

The vectors Rh186-189 (ΔUS8-11), and Rh182-185 (ΔUS2-6) were generated through BAC recombineering. BAC recombineering begins with recombination in *E. coli* between the RhCMV strain 68-1 BAC and a PCR product containing the SIV gag or SIVrtn marker and a kanamycin resistant (KanR) cassette. The KanR cassette is flanked by FRT sites, and the ends of the PCR product include between 40-60 base pairs of homology to the ORF to be deleted. Recombinants are selected with kanamycin, and are then subjected to arabinose-induced recombination of the FRT sites to delete the KanR cassette. Therefore, only a gag/rtn marker and a single FRT scar remain in place of the deleted ORF. This final BAC product is electroporated into rhesus fibroblasts, from which the recombinant virus is harvested. The viruses produced by this method and included in this study are diagrammed in FIGS. 4A and 4B.

Figure 5A:
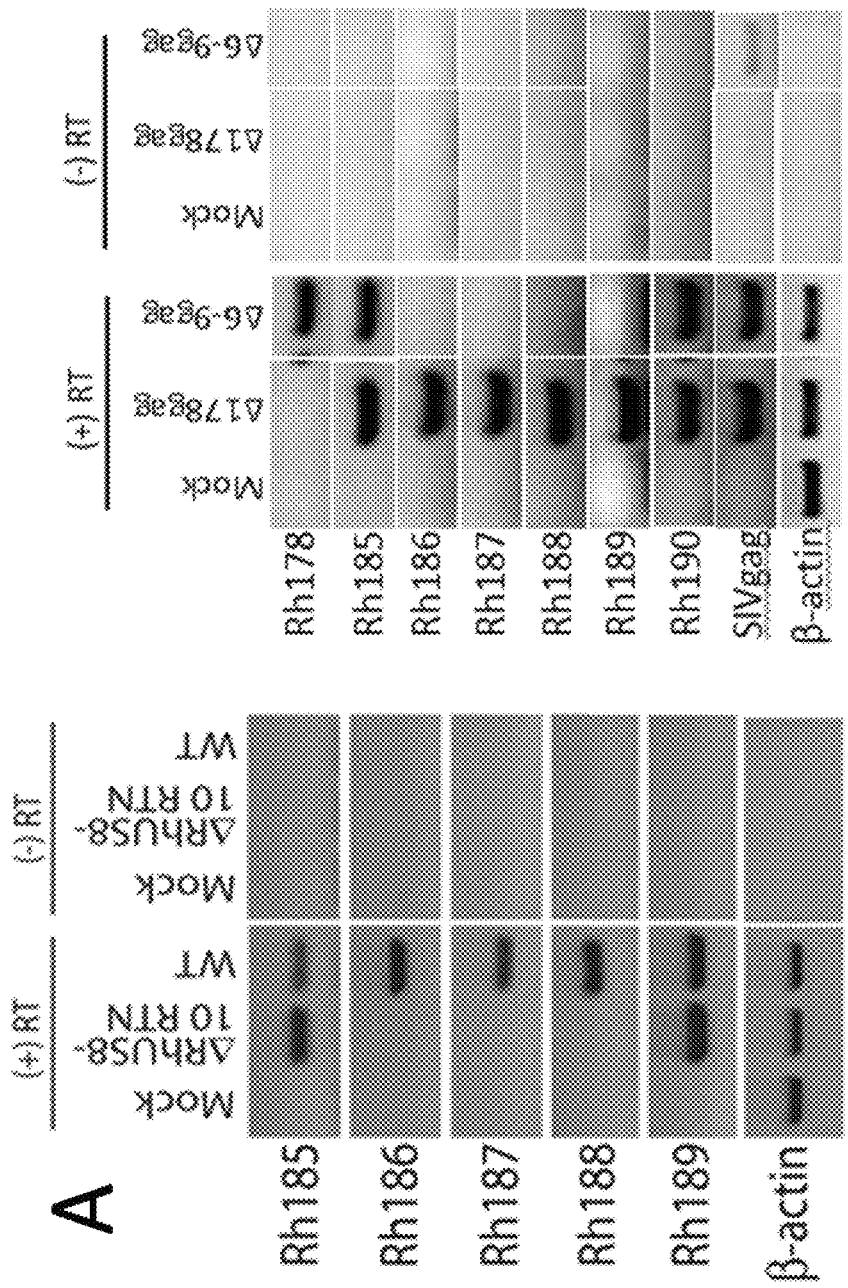
FIG. 5A depicts the characterization of recombinant RhCMVs by RT-PCR. Fibroblasts were infected at MOI=1 with the indicated virus and total RNA was harvested at 24 hpi (Δ6-9gag=ΔUS8-11gag). cDNA was synthesized by random hexamer priming, and transcripts were amplified with primers specific for the ORFs indicated on the left. Genes flanking the deleted regions were included to detect possible changes in transcription due to the deletions. WT=bacterial artificial chromosome (BAC)-derived wild type RhCMV. RT=reverse transcriptase.
Figure 5B:
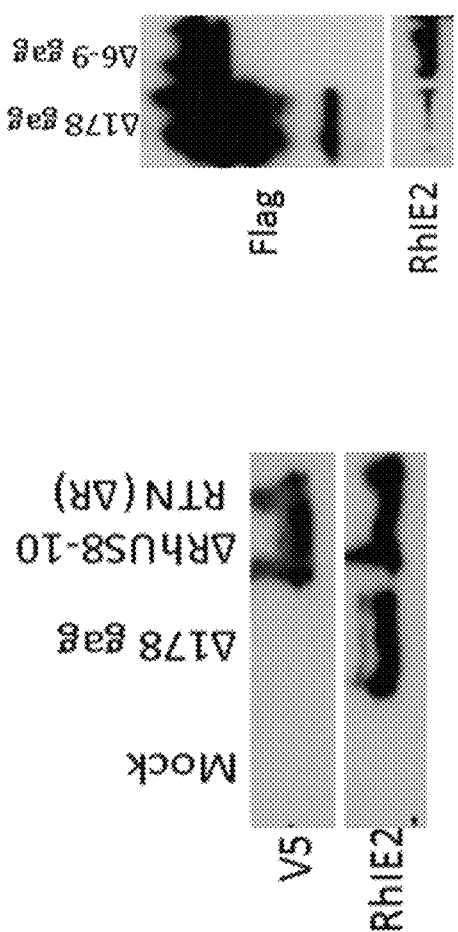
FIG. 5B depicts the expression of SIVgag and SIV RTN by recombinant viruses. Immunoblot analysis of FLAG-tagged SIVgag and V5-tagged SIV RTN was performed at the indicated times after fibroblasts were infected at MOI=1 and total lysate was harvested.

All viruses were thoroughly characterized in vitro. All recombinant BACs were screened by restriction digest to demonstrate an intact viral genome. BACs were also screened by PCR to ensure that the correct ORFs were deleted. Once viruses had been reconstituted from cell culture, their gene expression profiles, SIV protein marker expression, and growth kinetics were assayed. Semi-quantitative RT-PCR confirmed that the knockout strategy had deleted the appropriate ORFs without affecting surrounding transcripts or cellular controls GAPDH or β-actin (FIG. 5A). In addition, Western blot of infected cell lysate confirmed expression of either SIVgag or SIVrtn (tagged with Flag or V5, respectively). All infected cell lysates expressed viral protein IE-1 or IE-2 (FIG. 5B).

Figure 4A:
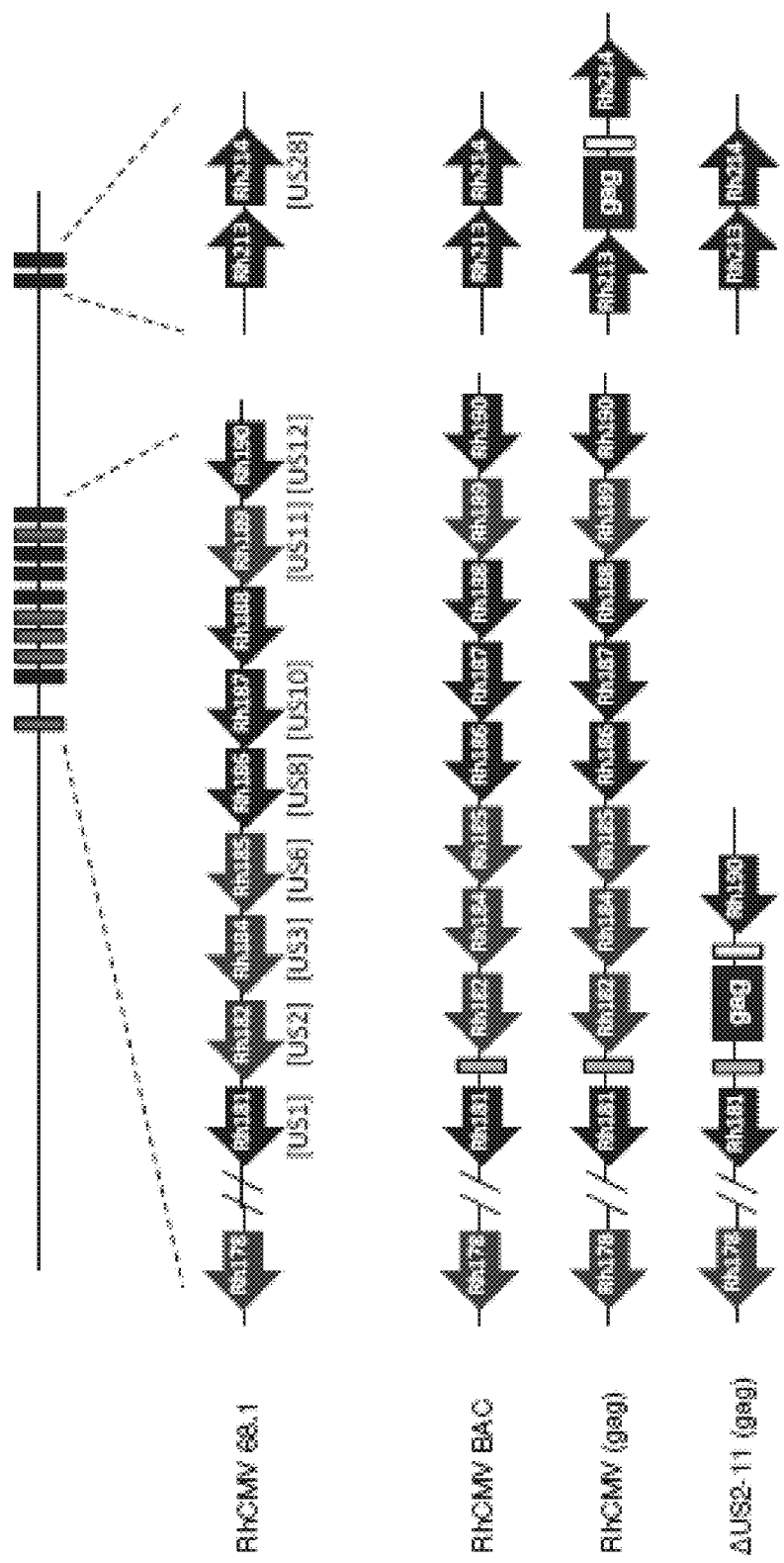
FIGS. 4A-4B depict a diagram of viruses used in Example 2. Regions of the genome that were altered to create mutant viruses are shown here in detail. All RhCMV ORFs are depicted as arrows that correspond to the direction of the ORF within the genome. Blue arrows represent genes that down regulate MHC class I. Designated RhCMV nomenclature is used for all ORFs. For ORFs with homology to HCMV genes the name of the corresponding HCMV homologue is shown in brackets. Also depicted are SIV immunological markers SIVgag and RTN, and recombination sites LoxP, FRT, and F5 FRT.
Figure 4B:
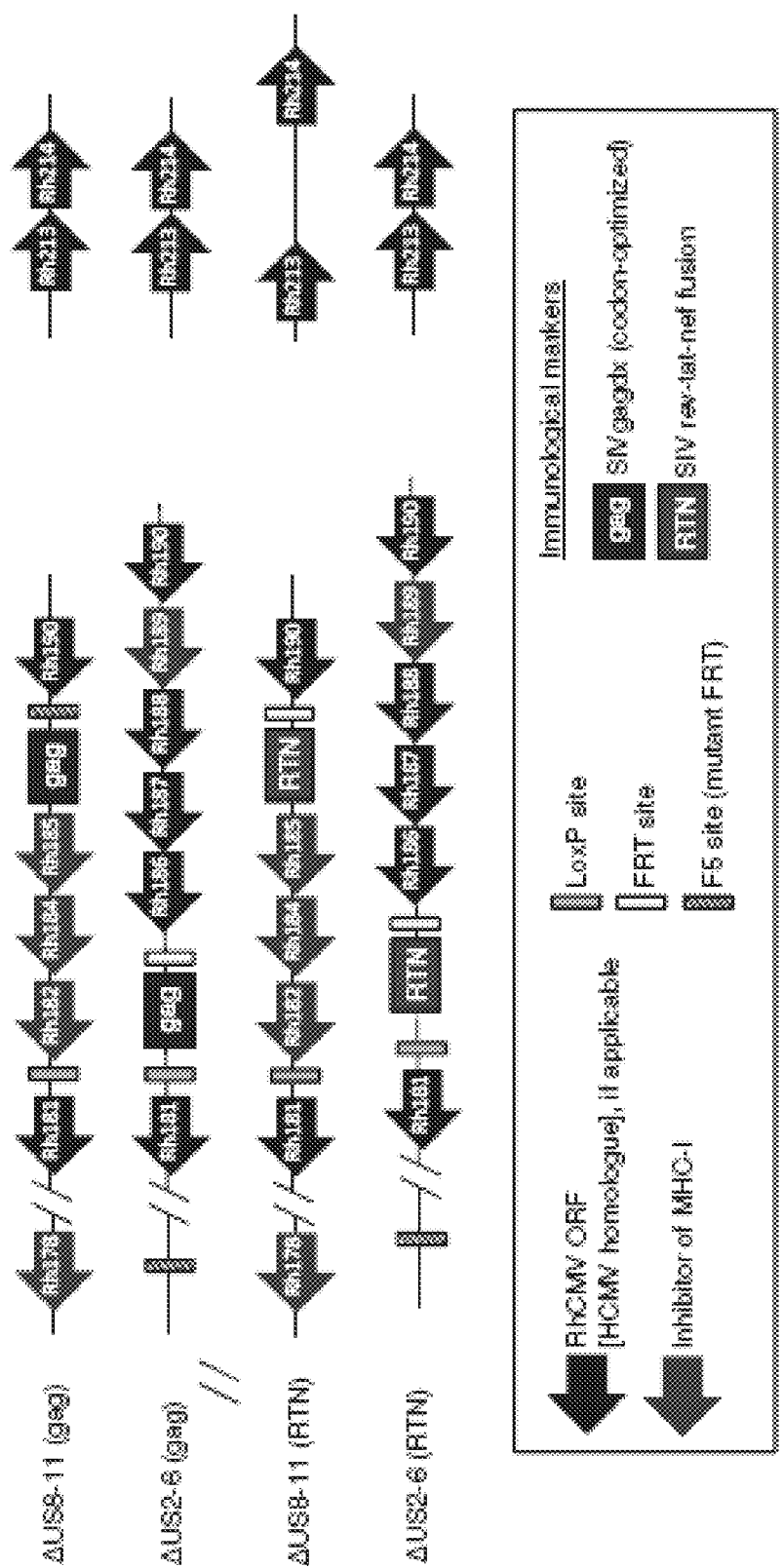

RhCMV lacking homologues of HCMV US8-11 causes superinfection and elicits gag-specific immunodominant responses. Applicants infected two Mamu A*01 RhCMV-seropositive rhesus macaques (RM) with a virus containing a targeted deletion within the Rh182-189 region that lacked the ORFs Rh186-Rh189 (corresponding to HCMV US8-11) but contained the exogenous antigen SIVgag driven by the EF1a promoter (ΔUS8-11gag) (FIGS. 4A and 4B). This virus still contains the majority of the MHC-I inhibitors, including homologues to HCMV US2, US3, and US6. The ΔUS8-11gag was able to overcome preexisting immunity to RhCMV and superinfect both Mamu A*01 RM, as determined by multiparameter flow cytometry of PBMCs and BAL collected from the two animals (FIG. 6A). In addition, both animals developed SIVgag-specific PBMC and BAL CD4+ and CD8+ T cells responses within 2 weeks of ΔUS8-11gag inoculation (FIG. 6B). The total SIVgag-specific T cell responses were measured by using a pool of overlapping peptides. Strikingly, both RM developed the same Mamu A*01-restricted SIVgag immunodominant responses seen with ΔUS2-11gag (FIGS. 1 and 6C). These data show that US8-11-deleted vectors can super-infect but also induce T cells to immunodominant epitopes.

Example 3—CMV Vectors Lacking US8-11 are Able to Super-Infect CMV-Positive Rhesus Macaques (RM) and CMV/SIV Vectors Lacking US8-11 Induce a Long-Term CD8+ T Cell Response to Typical Immune-Dominant SIV Epitopes Four CMV-positive RM were inoculated subcutaneously with $10^7$ plaque-forming units (PFU) of recombinant ΔUS8-

Figure 7A:
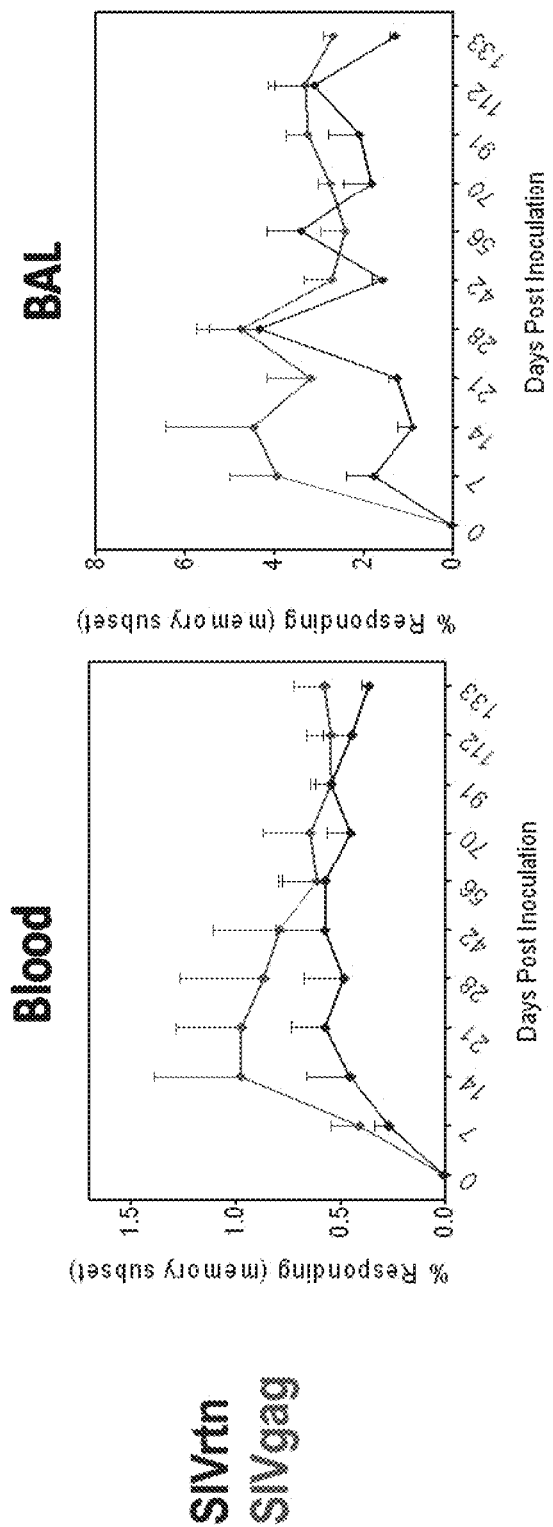
FIG. 7A is a line graph depicting the percentage of cells in the blood (left) and BAL (right) responding to SIVrtn and SIVgag in RM inoculated with ΔUS8-11RhCMV/rtn and ΔUS8-11RhCMV/gag vectors over time post inoculation.
Figure 7B:
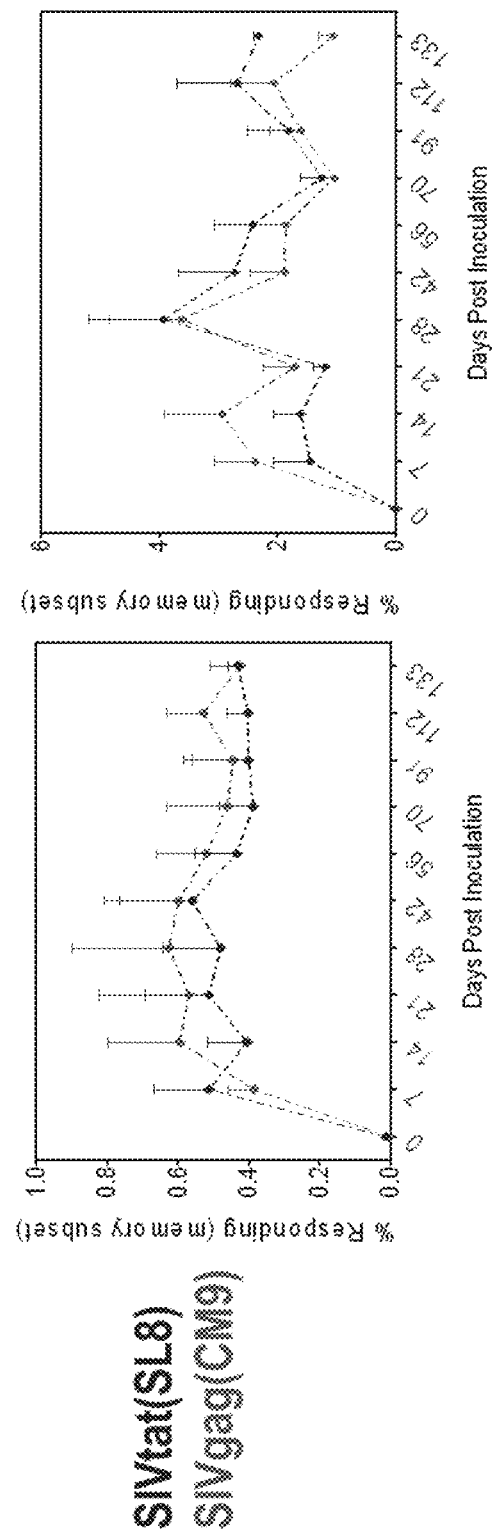
FIG. 7B is a line graph depicting the percentage of cells in the blood (left) and BAL (right) responding to the immunodominant Mamu A*01-restricted epitopes SIVtat (SL8) and SIVgag(CM9) determined by flow cytometric analysis in RM inoculated with ΔUS8-11RhCMV/rtn and ΔUS8-11RhCMV/gag vectors over time post inoculation.

11RhCMV/rtn and ΔUS8-11RhCMV/gag vector. Blood or BAL was collected at the indicated days and T cell responses were analyzed on the same day. In FIG. 7A, CD8+ T cell responses frequencies to the SIV antigens SIVgag and SIVrtn (fusion of rev-tat-nef) determined by flow cytometric analysis of intracellular cytokine staining for CD8+ T cells and the activation markers CD69, TNF-α and IFN-γ after stimulation of PBMC with overlapping peptides covering the SIV antigens. The percentage of the responding, SIVrtn or SIVgag-specific T cells within the overall memory subset in both the blood (left) and BAL (right) fractions are shown for each time point as the mean for all four RM (+/−SEM). The development and persistence of T cell responses against SIVrtn and SIVgag indicates the ability of US8-11-deleted vectors to super-infect CMV+ RM. In FIG. 7B, CD8+ T cell responses frequencies to the immunodominant Mamu A*01-restricted epitopes SIVtat(SL8) and SIVgag(CM9) determined by flow cytometric analysis of intracellular cytokine staining for CD8+ T cells and the activation markers CD69, TNF-α and IFN-γ after stimulation of PBMC with SL8 and CM9 9-mer peptides. The percentage of the responding, SIVtat(SL8) or SIVgag(CM9) specific T cells within the overall memory subset in both the blood (left) and BAL (right) fractions are shown for each time point as the mean for all four RM (+/−SEM). The development of T cell responses against immunodominant epitopes tatSL8 and gagCM9 indicates the ability of US8-11-deleted vectors to elicit CD8+ T cell responses to immunodominant epitopes that are not targeted for CD8+ T cell responses by wildtype RhCMVrtn- or RhCMgag-expressing vectors.

Figure 8A:
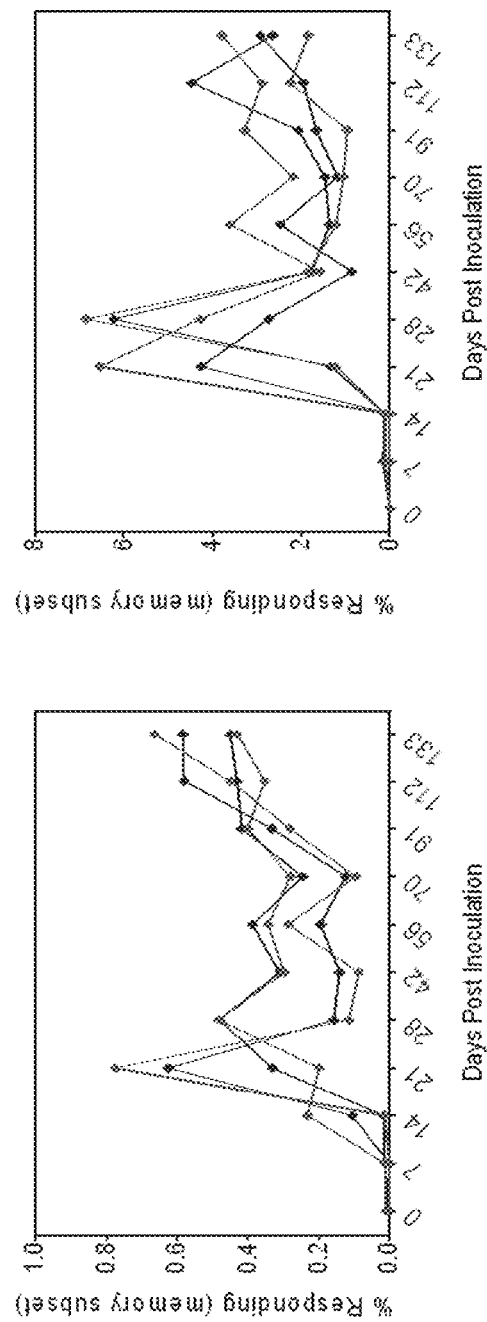
FIG. 8A is a line graph depicting the percentage of cells in the blood (left) and BAL (right) responding to SIVrtn and SIVgag in RM inoculated with ΔUS2-6RhCMV/rtn and ΔUS2-6RhCMV/gag vectors over time post inoculation.
Figure 8B:
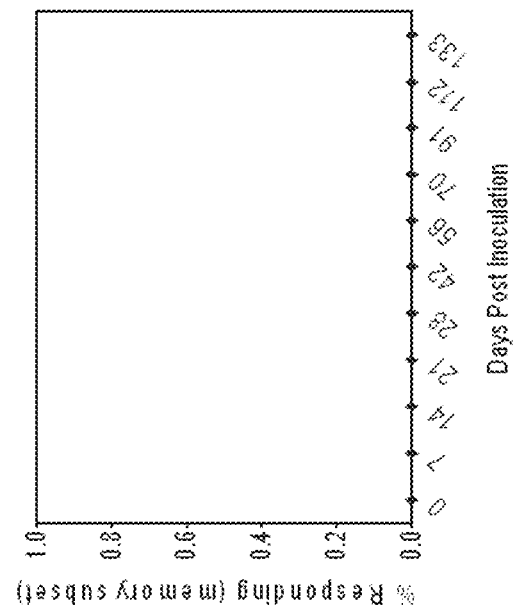
FIG. 8B is a line graph depicting the percentage of cells in the blood (left) and BAL (right) responding to the immunodominant Mamu A*01-restricted epitopes SIVtat (SL8) and SIVgag(CM9) determined by flow cytometric analysis in RM inoculated with ΔUS2-6RhCMV/rtn and ΔUS2-6RhCMV/gag vectors over time post inoculation. No responding cells were detected.
Figure 8B:
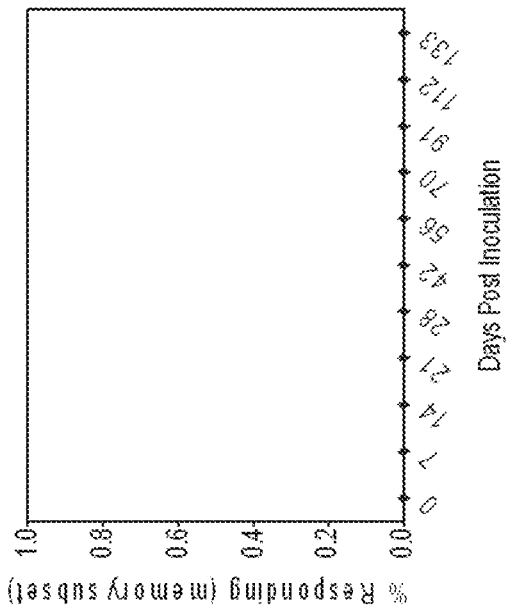

Example 4—CMV Vectors Lacking US2-6 are Able to Super-Infect CMV-Positive Rhesus Macaques (RM) but do not Induce a CD8+ T Cell Response to Typical Immune-Dominant SIV Epitopes Four CMV-positive RM were inoculated subcutaneously with $10^7$ plaque-forming units (PFU) of recombinant ΔUS2-6RhCMV/rtn and ΔUS2-6RhCMV/gag vector. Blood or BAL was collected at the indicated days and T cell responses were analyzed on the same day. In FIG. 8A, CD8+ T cell responses frequencies to the SIV antigens SIVgag and SIVrtn (fusion of rev-tat-nef) determined by flow cytometric analysis of intracellular cytokine staining for CD8+ T cells and the activation markers CD69, TNF-α and IFN-γ after stimulation of PBMC with overlapping peptides covering the SIV antigens. The percentage of the responding, SIVrtn or SIVgag-specific T cells within the overall memory subset in the blood (left) and BAL (right) fractions are shown for each time point as the mean for all four RM (+/−SEM). The development and persistence of T cell responses against SIVrtn and SIVgag indicates the ability of US2-6-deleted vectors to super-infect CMV+ RM. In FIG. 7B, CD8+ T cell responses frequencies to the immunodominant Mamu A*01-restricted epitopes SIVtat(SL8) and SIVgag(CM9) determined by flow cytometric analysis of intracellular cytokine staining for CD8+ T cells and the activation markers CD69, TNF-α and IFN-γ after stimulation of PBMC with SL8 and CM9 9-mer peptides. The percentage of the responding, SIVtat(SL8) or SIVgag(CM9) specific T cells within the overall memory subset in the blood (left) and BAL (right) fractions are shown for each time point as the mean for all four RM (+/−SEM). The lack of T cell responses against immunodominant epitopes tatSL8 and gagCM9 indicates that US2-6-deleted vectors are unable to induce CD8+ T cell responses to immunodominant epitopes similar to wildtype RhCMVrtn- or RhCMgag-expressing vectors.

Example 5—Deletion of Rh189(US11) by Gag-insertion in RhCMV-retanef

Figure 9A:
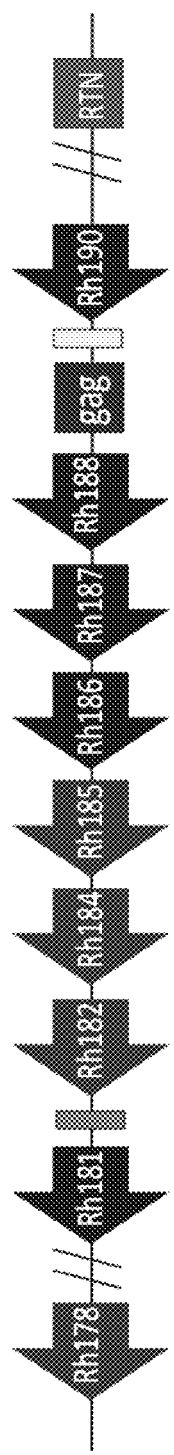
FIG. 9A is a schematic representation of the construct RTNA189gag.

FIG. 9A shows a schematic representation of the construct RTNΔ189gag. The inhibitor of antigen presentation Rh189 (US11) was deleted by insertion of a promoterless SIVgag. SIVretanef was inserted between Rh213 and 214 and is driven by the EF1α promoter as described (Hansen et al. Nat. Med. 2009).

Figure 9B:
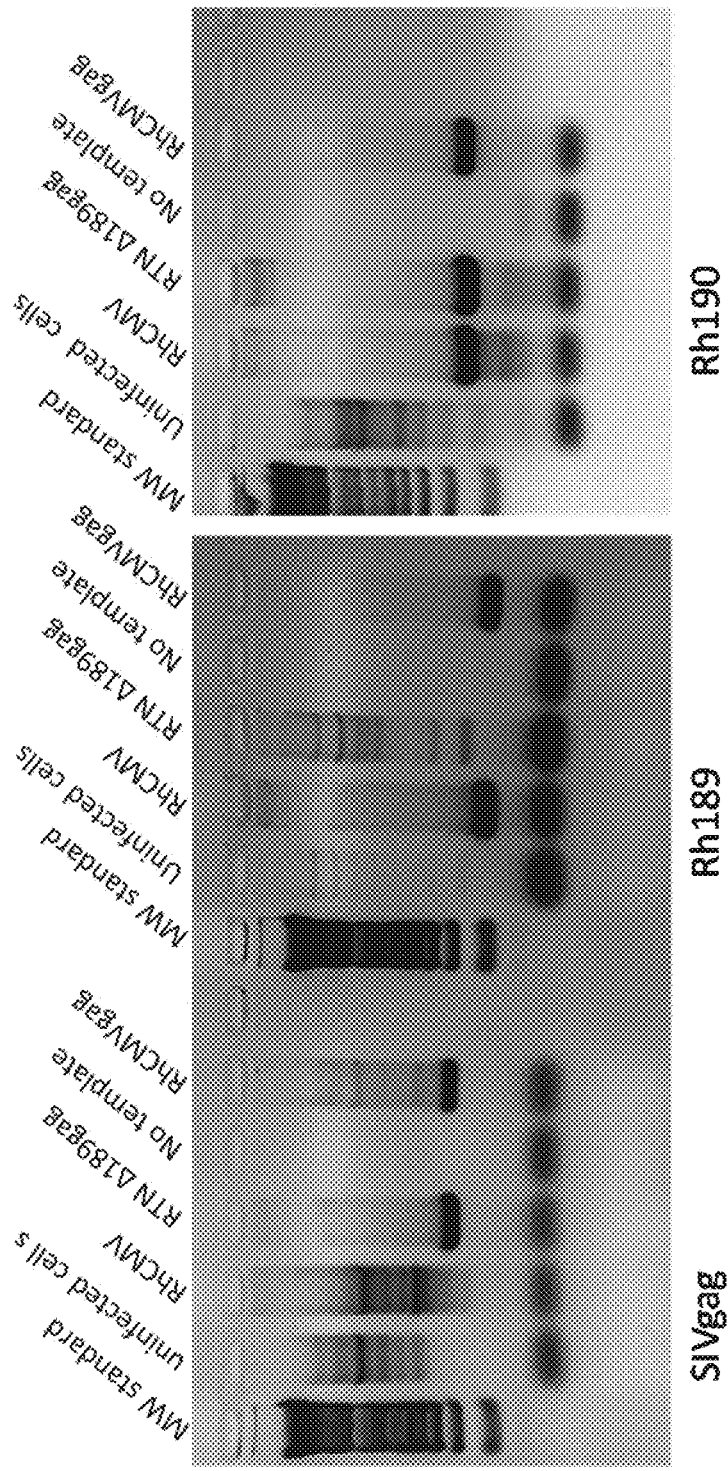
FIG. 9B is an image of a gel that shows the results of PCR amplification of the constructs of FIG. 9A verifying Rh189-deletion and SIVgag insertion.

FIG. 9B shows a verification of Rh189-deletion and SIVgag insertion by polymerase chain reaction. Lysates of rhesus fibroblasts uninfected or infected with the indicated viruses were subjected to PCR using primers specific for the indicated inserts. Note that construct RTNΔRh189gag does not yield a Rh189-specific DNA fragment, only non-specific bands also found in uninfected cells. In contrast, probing for SIVgag or for the neighboring open reading frame Rh190 results in a specific PCR product.

Figure 9C:
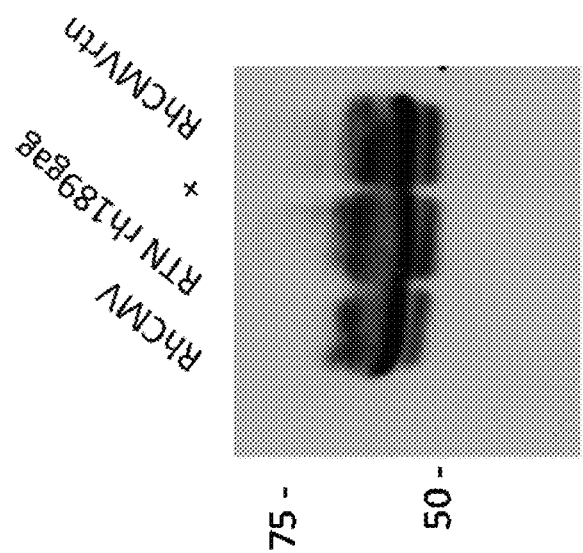
FIG. 9C is an image of an immunoblot probing for SIVretanef in the indicated constructs.

FIG. 9C shows an Immunoblot for SIVretanef. Lysates of fibroblasts infected with the indicated viruses were separated by SDS-PAGE and after transfer onto immunoblot membranes probed with an antibody against the V5-epitope that is fused to the rev-tat-nef (rtn) fusion protein of SIV. Note that only in viruses expressing SIVrtn the respective protein is detectable.

Example 6—FIG. 10: RhCMV Lacking Rh189(US11) is Able to Super-infect CMV+ Animals and Induces an Immune Response Against Immunodominant SIV Epitopes A CMV-positive RM was inoculated subcutaneously with $10^7$ plaque-forming units (PFU) of recombinant RhCMV/RTNΔ189gag. The Figure shows CD8+ T cell responses frequencies to overlapping peptides of SIVrtn a fusion of rev/tat and nef or against the immunodominant Mamu A*01-restricted epitope SL8 of SIVtat as determined by flow cytometric analysis of intracellular cytokine staining for CD8+ T cells and the activation markers TNF-α and IFN-γ after stimulation of peripheral blood (top panels) and BAL T cells (bottom panels) with peptides. Depicted are T cells from a representative RM responding to SIVrtn (left panels) or SIVtat(SL8) (right panels). The upper and lower right quadrants of the flow cytometric profiles indicate the net percentage of the total CD8+ T cell population responding to the designated antigen with production of both TNF and IFN-γ or TNF alone, respectively.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method of eliciting an immune response to at least one immunodominant epitope of at least one heterologous antigen in a cytomegalovirus (CMV)-seropositive subject in need thereof, the method comprising administering a recombinant CMV vector encoding the at least one heterologous antigen to the CMV-seropositive subject in an amount effective to elicit a long-term CD8+ T cell response to the at least one immunodominant epitope,
wherein the recombinant CMV vector does not express an active US11 protein or a functional homologue thereof, and
wherein the recombinant CMV vector encodes functional US2, US3, and US6 proteins, or functional homologues thereof.

2. The method of claim 1, wherein the at least one heterologous antigen comprises an infectious disease antigen or a tumor antigen.

3. The method of claim 1, wherein the CMV-seropositive subject is a human or a rhesus macaque.

4. The method of claim 1, wherein the recombinant CMV vector comprises one or more of: (1) a point mutation in a nucleic acid sequence encoding US11 or a functional homologue thereof, (2) a frameshift mutation in the nucleic acid sequence encoding US11 or a functional homologue thereof, or (3) a deletion of all or part of the nucleic acid sequence encoding US11 or a functional homologue thereof.

5. The method of claim 1, wherein administering comprises intravenous, intramuscular, intraperitoneal, or oral administration of the recombinant CMV vector.

6. The method of claim 1, wherein the at least one heterologous antigen is selected from the group consisting of: a Hepatitis B virus antigen; a Hepatitis C virus antigen; a human immunodeficiency virus (HIV) antigen; a simian immunodeficiency virus (SIV) antigen; a *Clostridium tetani* antigen; a *Mycobacterium tuberculosis* antigen; and a *Plasmodium* antigen.

7. The method of claim 1, wherein expression of the at least one heterologous antigen is driven by a heterologous antigen-encoding sequence operably linked to a promoter.

8. The method of claim 7, wherein the promoter is selected from the group consisting of: a constitutive promoter, an inducible promoter, a non-viral promoter, and a viral promoter.

9. The method of claim 4, wherein the recombinant CMV vector comprises a deletion of all of the nucleic acid sequence encoding US11 or a functional homologue thereof.

10. The method of claim 1, wherein the recombinant CMV vector encodes the US2 of SEQ ID NO:1, the US3 of SEQ ID NO:2, and the US6 of SEQ ID NO:3.

11. The method of claim 1, wherein the at least one heterologous antigen comprises an infectious disease antigen or a tumor antigen,
wherein the CMV-seropositive subject is a human cytomegalovirus (HCMV)-seropositive human subject, and
wherein the recombinant CMV vector is a recombinant HCMV vector.

12. The method of claim 8, wherein the promoter is an EF1-alpha promoter or a CMV-IE promoter.

13. The method of claim 1, wherein the at least one heterologous antigen comprises an infectious disease antigen or tumor antigen,
wherein the CMV-seropositive subject is a HCMV-seropositive human subject,
wherein the recombinant CMV vector is a recombinant HCMV vector, and
wherein the recombinant HCMV vector does not express an active US8 or US10 protein.

14. The method of claim 13, wherein the recombinant HCMV vector does not express active US8 and US10 proteins.

15. The method of claim 14, wherein the recombinant HCMV vector comprises a deletion of all of the nucleic acid sequence encoding US8-US11.

16. The method of claim 1, wherein the recombinant CMV vector does not express an active US8 or US10 protein, or a functional homologue thereof.

17. The method of claim 16, wherein the recombinant CMV vector does not express active US8 and US10 proteins, or functional homologues thereof.

18. The method of claim 17, wherein the recombinant CMV vector comprises a deletion of all of the nucleic acid sequence encoding US8-US11 or functional homologues thereof.

19. The method of claim 1, wherein the recombinant CMV vector is a recombinant rhesus CMV (RhCMV) vector.

20. The method of claim 13, wherein the at least one heterologous antigen is selected from the group consisting of: an HIV antigen, an SIV antigen, a hepatitis B virus antigen, a hepatitis C virus antigen, a *Clostridium tetani* antigen, *Mycobacterium tuberculosis* antigen, and a *plasmodium* antigen.

21. The method of claim 11, wherein the at least one heterologous antigen is selected from the group consisting of: an HIV antigen, an SIV antigen, a hepatitis B virus antigen, a hepatitis C virus antigen, a *Clostridium tetani* antigen, a *Mycobacterium tuberculosis* antigen, and a *plasmodium* antigen.

22. A method of eliciting an immune response to at least one immunodominant epitope of at least one heterologous antigen in a CMV-seropositive subject in need thereof, the method comprising administering a recombinant CMV vector to the CMV-seropositive subject in an amount effective to elicit a long-term CD8+ T cell response to the at least one immunodominant epitope;
wherein the recombinant CMV vector does not express an active US11 protein or a functional homologue thereof;
wherein the recombinant CMV vector comprises: a nucleic acid sequence encoding functional US2, US3, and US6 proteins, or functional homologues thereof; a nucleic acid sequence encoding US12 or a functional homologue thereof; and a nucleic acid sequence encoding the at least one heterologous antigen; and
wherein the nucleic acid sequence encoding the at least one heterologous antigen is located between the nucleic acid sequence encoding US6 or a functional homologue thereof and the nucleic acid sequence encoding US12 or a functional homologue thereof.

23. The method of claim 22, wherein the CMV-seropositive subject is a human or a rhesus macaque.

24. The method of claim 22, wherein the recombinant CMV vector is a recombinant HCMV vector or a recombinant RhCMV vector.

25. The method of claim 22, wherein the recombinant CMV vector comprises a deletion of all of the nucleic acid sequence encoding US8, US10, and US11, or functional homologues thereof.

26. The method of claim 22, wherein the nucleic acid sequence encoding the at least one heterologous antigen is located between the nucleic acid sequence encoding US8 or a functional homologue thereof and the nucleic acid sequence encoding US12 or a functional homologue thereof.

27. The method of claim 26, wherein the recombinant CMV vector comprises a deletion of all of the nucleic acid sequence encoding US10 and US11, or functional homologues thereof.

28. The method of claim 22, wherein the nucleic acid sequence encoding the at least one heterologous antigen is located between the nucleic acid sequence encoding US10 or a functional homologue thereof and the nucleic acid sequence encoding US12 or a functional homologue thereof.

29. The method of claim 22, wherein the at least one heterologous antigen comprises an infectious disease antigen or a tumor antigen.

30. The method of claim 22, wherein the at least one heterologous antigen is selected from the group consisting of: an HIV antigen, an SIV antigen, a hepatitis B virus antigen, a hepatitis C virus antigen, a *Clostridium tetani* antigen, a *Mycobacterium tuberculosis* antigen, and a *plasmodium* antigen.

31. A method of eliciting an immune response to at least one immunodominant epitope of at least one heterologous antigen in a HCMV-seropositive subject in need thereof, the method comprising administering a recombinant HCMV vector to the HCMV-seropositive subject in an amount effective to elicit a long-term CD8+ T cell response to the at least one immunodominant epitope;
wherein the recombinant HCMV vector does not express an active US11 protein or a functional homologue thereof;
wherein the recombinant HCMV vector comprises: a nucleic acid sequence encoding functional US2, US3, and US6 proteins; a nucleic acid sequence encoding US12; and a nucleic acid sequence encoding the at least one heterologous antigen; and
wherein the nucleic acid sequence encoding the at least one heterologous antigen is located between the nucleic acid sequence encoding US6 and the nucleic acid sequence encoding US12.

32. The method of claim 31, wherein the at least one heterologous antigen comprises an infectious disease antigen or a tumor antigen.

33. The method of claim 31, wherein the at least one heterologous antigen is selected from the group consisting of: a hepatitis B virus antigen, a hepatitis C virus antigen, a *Clostridium tetani* antigen, a *Mycobacterium tuberculosis* antigen, and a *Plasmodium* antigen.

34. A method of eliciting an immune response to at least one immunodominant epitope of at least one heterologous antigen in a HCMV-seropositive subject in need thereof, the method comprising administering a recombinant HCMV vector encoding the at least one heterologous antigen to the HCMV-seropositive subject in an amount effective to elicit a long-term CD8+ T cell response to the at least one immunodominant epitope,
wherein the at least one heterologous antigen is a herpes simplex virus (HSV) antigen or a human papillomavirus antigen,
wherein the recombinant HCMV vector does not express an active US11 protein, and
wherein the recombinant HCMV vector encodes functional US2, US3, and US6 proteins.

35. The method of claim 34, wherein the at least one heterologous antigen is a human papillomavirus antigen.

36. The method of claim 34, wherein the at least one heterologous antigen is a HSV antigen.

37. The method of claim 36, wherein the HSV antigen is an HSV-1 antigen.

38. The method of claim 36, wherein the HSV antigen is an HSV-2 antigen.

39. The method of claim 34, wherein the recombinant HCMV vector comprises one or more of: (1) a point mutation in a nucleic acid sequence encoding US11, (2) a frameshift mutation in the nucleic acid sequence encoding US11, or (3) a deletion of all or part of the nucleic acid sequence encoding US11.

40. The method of claim 39, wherein the recombinant HCMV vector comprises a deletion of all of the nucleic acid sequence encoding US11.

41. The method of claim 34, wherein administering comprises intravenous, intramuscular, intraperitoneal, or oral administration of the recombinant HCMV vector.

42. The method of claim 34, wherein expression of the at least one heterologous antigen is driven by a heterologous antigen-encoding sequence operably linked to a promoter.

43. The method of claim 42, wherein the promoter is selected from the group consisting of: a constitutive promoter, an inducible promoter, a non-viral promoter, and a viral promoter.

44. The method of claim 43, wherein the promoter is an EF1-alpha promoter or a CMV-IE promoter.

45. The method of claim 34, wherein the recombinant HCMV vector does not express an active US8 or US10 protein.

46. The method of claim 45, wherein the recombinant HCMV vector does not express active US8 and US10 proteins.

47. The method of claim 46, wherein the recombinant HCMV vector comprises a deletion of all of the nucleic acid sequence encoding US8-US11.

48. The method of claim 34, wherein the recombinant HCMV vector encodes the US2 of SEQ ID NO:1, the US3 of SEQ ID NO:2, and the US6 of SEQ ID NO:3.

49. The method of claim 34, wherein the recombinant HCMV vector further comprises a nucleic acid sequence encoding US12, wherein the nucleic acid sequence encoding the at least one heterologous antigen is located between the nucleic acid sequence encoding US6 and the nucleic acid sequence encoding US12.

50. The method of claim 49, wherein the recombinant HCMV vector comprises a deletion of all of the nucleic acid sequence encoding US8, US10, and US11.

51. The method of claim 49, wherein the recombinant HCMV vector further comprises a nucleic acid encoding US8.

52. The method of claim 51, wherein the nucleic acid sequence encoding the at least one heterologous antigen is located between the nucleic acid sequence encoding US8 and the nucleic acid sequence encoding US12.

53. The method of claim 52, wherein the recombinant HCMV vector comprises a deletion of all of the nucleic acid sequence encoding US10 and US11.

54. The method of claim 51, wherein the recombinant HCMV vector further comprises a nucleic acid encoding US10.

55. The method of claim 54, wherein the nucleic acid sequence encoding the at least one heterologous antigen is located between the nucleic acid sequence encoding US10 and the nucleic acid sequence encoding US12.

* * * * *

UNITED STATES PATENT AND TRADEMARK OFFICE
CERTIFICATE OF CORRECTION

PATENT NO. : 9,862,972 B2
APPLICATION NO. : 14/086602
DATED : January 9, 2018
INVENTOR(S) : Louis Picker, Klaus Früh and Scott Hansen Page 1 of 1

It is certified that error appears in the above-identified patent and that said Letters Patent is hereby corrected as shown below:

In the Specification

At Column 1, Lines 18-23, please delete the following header and paragraph:
"FEDERAL FUNDING LEGEND
This invention was supported in part by the National Institutes of Health grant number ROI AI059457. The federal government may have certain rights to this invention."

And replace it with:
-- GOVERNMENT SUPPORT
This invention was made with government support under AI059457 awarded by the National Institutes of Health. The government has certain rights in the invention. --

Signed and Sealed this
Twenty-third Day of July, 2019

Andrei Iancu
*Director of the United States Patent and Trademark Office*

SEQUENCE LISTING

<160> NUMBER OF SEQ ID NOS: 4

<210> SEQ ID NO 1
<211> LENGTH: 199
<212> TYPE: PRT
<213> ORGANISM: Cytomegalovirus

<400> SEQUENCE: 1

Met Asn Asn Leu Trp Lys Ala Trp Val Gly Leu Trp Thr Ser Met Gly
1               5                   10                  15

Pro Leu Ile Arg Leu Pro Asp Gly Ile Thr Lys Ala Gly Glu Asp Ala
            20                  25                  30

Leu Arg Pro Trp Lys Ser Thr Ala Lys His Pro Trp Phe Gln Ile Glu
        35                  40                  45

Asp Asn Arg Cys Tyr Ile Asp Asn Gly Lys Leu Phe Ala Arg Gly Ser
    50                  55                  60

Ile Val Gly Asn Met Ser Arg Phe Val Phe Asp Pro Lys Ala Asp Tyr
65                  70                  75                  80

Gly Gly Val Gly Glu Asn Leu Tyr Val His Ala Asp Asp Val Glu Phe
                85                  90                  95

Val Pro Gly Glu Ser Leu Lys Trp Asn Val Arg Asn Leu Asp Val Met
            100                 105                 110

Pro Ile Phe Glu Thr Leu Ala Leu Arg Leu Val Leu Gln Gly Asp Val
        115                 120                 125

Ile Trp Leu Arg Cys Val Pro Glu Leu Arg Val Asp Tyr Thr Ser Ser
    130                 135                 140

Ala Tyr Met Trp Asn Met Gln Tyr Gly Met Val Arg Lys Ser Tyr Thr
145                 150                 155                 160

His Val Ala Trp Thr Ile Val Phe Tyr Ser Ile Asn Ile Thr Leu Leu
                165                 170                 175

Val Leu Phe Ile Val Tyr Val Thr Val Asp Cys Asn Leu Ser Met Met
            180                 185                 190

Trp Met Arg Phe Phe Val Cys
        195

<210> SEQ ID NO 2
<211> LENGTH: 186
<212> TYPE: PRT
<213> ORGANISM: Cytomegalovirus

<400> SEQUENCE: 2

Met Lys Pro Val Leu Val Leu Ala Ile Leu Ala Val Leu Phe Leu Arg
1               5                   10                  15

Leu Ala Asp Ser Val Pro Arg Pro Leu Asp Val Val Ser Glu Ile
            20                  25                  30

Arg Ser Ala His Phe Arg Val Glu Glu Asn Gln Cys Trp Phe His Met
        35                  40                  45

Gly Met Leu His Tyr Lys Gly Arg Met Ser Gly Asn Phe Thr Glu Lys
    50                  55                  60

His Phe Val Ser Val Gly Ile Val Ser Gln Ser Tyr Met Asp Arg Leu
65                  70                  75                  80

Gln Val Ser Gly Glu Gln Tyr His His Asp Glu Arg Gly Ala Tyr Phe
                85                  90                  95

Glu Trp Asn Ile Gly Gly His Pro Val Pro His Thr Val Asp Met Val
            100                 105                 110

```
Asp Ile Thr Leu Ser Thr Arg Trp Gly Asp Pro Lys Lys Tyr Ala Ala
            115                 120                 125

Cys Val Pro Gln Val Arg Met Asp Tyr Ser Ser Gln Thr Ile Asn Trp
130                 135                 140

Tyr Leu Gln Arg Ser Ile Arg Asp Asp Asn Trp Gly Leu Leu Phe Arg
145                 150                 155                 160

Thr Leu Leu Val Tyr Leu Phe Ser Leu Val Leu Val Leu Leu Thr
                165                 170                 175

Val Gly Val Ser Ala Arg Leu Arg Phe Ile
            180                 185

<210> SEQ ID NO 3
<211> LENGTH: 183
<212> TYPE: PRT
<213> ORGANISM: Cytomegalovirus

<400> SEQUENCE: 3

Met Asp Leu Leu Ile Arg Leu Gly Phe Leu Leu Met Cys Ala Leu Pro
1               5                   10                  15

Thr Pro Gly Glu Arg Ser Ser Arg Asp Pro Ile Thr Leu Leu Ser Leu
            20                  25                  30

Ser Pro Arg Gln Gln Ala Cys Val Pro Arg Thr Lys Ser Tyr Arg Pro
        35                  40                  45

Val Cys Tyr Asn Asp Thr Gly Asp Cys Thr Asp Ala Asp Asp Ser Trp
50                  55                  60

Lys Gln Leu Ser Glu Asp Phe Ala His Gln Cys Leu Gln Ala Ala Lys
65                  70                  75                  80

Lys Arg Pro Lys Thr His Lys Ser Arg Pro Asn Asp Arg Asn Leu Glu
                85                  90                  95

Gly Arg Leu Thr Cys Gln Arg Val Ser Arg Leu Leu Pro Cys Asp Leu
            100                 105                 110

Asp Ile His Pro Ser His Arg Leu Leu Thr Leu Met Asn Asp Cys Val
        115                 120                 125

Cys Asp Gly Ala Val Trp Asn Ala Phe Arg Leu Ile Glu Arg His Gly
130                 135                 140

Phe Phe Ala Val Thr Leu Tyr Leu Cys Cys Gly Ile Thr Leu Leu Val
145                 150                 155                 160

Val Ile Leu Ala Leu Leu Cys Ser Ile Thr Tyr Glu Ser Thr Gly Arg
                165                 170                 175

Gly Ile Arg Arg Cys Gly Ser
            180

<210> SEQ ID NO 4
<211> LENGTH: 215
<212> TYPE: PRT
<213> ORGANISM: Cytomegalovirus

<400> SEQUENCE: 4

Met Asn Leu Val Met Leu Ile Leu Ala Leu Trp Ala Pro Val Ala Gly
1               5                   10                  15

Ser Met Pro Glu Leu Ser Leu Thr Leu Phe Asp Glu Pro Pro Pro Leu
            20                  25                  30

Val Glu Thr Glu Pro Leu Pro Pro Leu Pro Asp Val Ser Glu Tyr Arg
        35                  40                  45

Val Glu Ser Ser Glu Ala Arg Cys Val Leu Arg Ser Gly Gly Arg Leu
50                  55                  60
```

-continued

```
Glu Ala Leu Trp Thr Leu Arg Gly Asn Leu Ser Val Pro Thr Pro Thr
 65              70                  75                  80

Pro Arg Val Tyr Tyr Gln Thr Leu Glu Gly Tyr Ala Asp Arg Val Pro
             85                  90                  95

Thr Pro Val Glu Asp Val Ser Glu Ser Leu Val Ala Lys Arg Tyr Trp
            100                 105                 110

Leu Arg Asp Tyr Arg Val Pro Gln Arg Thr Lys Leu Val Leu Phe Tyr
        115                 120                 125

Phe Ser Pro Cys His Gln Cys Gln Thr Tyr Tyr Val Glu Cys Glu Pro
        130                 135                 140

Arg Cys Leu Val Pro Trp Val Pro Leu Trp Ser Ser Leu Glu Asp Ile
145                 150                 155                 160

Glu Arg Leu Leu Phe Glu Asp Arg Arg Leu Met Ala Tyr Tyr Ala Leu
                165                 170                 175

Thr Ile Lys Ser Ala Gln Tyr Thr Leu Met Met Val Ala Val Ile Gln
                180                 185                 190

Val Phe Trp Gly Leu Tyr Val Lys Gly Trp Leu His Arg His Phe Pro
            195                 200                 205

Trp Met Phe Ser Asp Gln Trp
    210                 215
```